(12) United States Patent
Dierlamm et al.

(10) Patent No.: US 7,807,809 B2
(45) Date of Patent: *Oct. 5, 2010

(54) MOLECULAR CHARACTERIZATION OF CHROMOSOME TRANSLOCATION T(11;18)(Q21;Q21) AND ITS CORRELATION TO CARCINOGENESIS

(75) Inventors: Judith Dierlamm, Hamburg (DE); Mathijs Baens, Lubbeek (BE); Peter Marijnen, Herent (BE)

(73) Assignee: Vlaams Interuniversitair Instituut voor Biotechnologie VZW, Ghent (BE)

( * ) Notice: Subject to any disclaimer, the term of this patent is extended or adjusted under 35 U.S.C. 154(b) by 723 days.

This patent is subject to a terminal disclaimer.

(21) Appl. No.: 10/353,461

(22) Filed: Jan. 28, 2003

(65) Prior Publication Data

US 2003/0176682 A1 Sep. 18, 2003

Related U.S. Application Data

(63) Continuation of application No. 09/579,692, filed on May 26, 2000, now Pat. No. 6,689,875.

(60) Provisional application No. 60/138,834, filed on Jun. 9, 1999.

(51) Int. Cl.
*C07H 21/04* (2006.01)
*C12N 15/00* (2006.01)
*A61K 31/70* (2006.01)

(52) U.S. Cl. ............... 536/23.4; 536/23.1; 536/24.3; 435/320.1

(58) Field of Classification Search .......... 536/2.1, 536/23.4, 24.3, 24.31, 24.5; 435/91.2
See application file for complete search history.

(56) References Cited

U.S. PATENT DOCUMENTS

| | | | |
|---|---|---|---|
| 4,701,409 A | 10/1987 | Croce | |
| 5,242,795 A | 9/1993 | Croco | |
| 5,487,970 A * | 1/1996 | Rowley et al. | 435/6 |
| 5,919,912 A * | 7/1999 | Korneluk et al. | 530/389.2 |
| 6,607,879 B1 * | 8/2003 | Cocks et al. | 435/6 |
| 6,689,875 B1 * | 2/2004 | Dierlamm et al. | 536/23.4 |
| 6,783,961 B1 * | 8/2004 | Edwards et al. | 435/91.1 |

FOREIGN PATENT DOCUMENTS

| | | |
|---|---|---|
| EP | 0 189 628 | 8/1986 |
| WO | WO 91/00364 | 1/1991 |
| WO | WO 97/06182 | 2/1997 |
| WO | WO 00/73500 A1 | 12/2000 |

OTHER PUBLICATIONS

Dierlamm et al. The apoptosis inhibitor gene API2 and a novel 18q gene, MLT, are recurrently rearranged in the t(11;18) (q21;q21) associated with mucosa-associated lymphoid tissue lymphomas. Blood: 93, No. 11 Jun. 1, 1999, pp. 3601-3609.*

Griffin et al. t(11;18)(q21;q21) is a recurrent chromosome abnormality in small lymphocytic lymphoma. Genes, Chromosomes & Cancer 4:153-157,1992.*

GenBank Accession No. AA826328, Jun. 9, 1998.*

Stoffel et al. Chromosome 18 breakpoint in t(11;18)(q21;q21) translocation associated with MALT lymphoma is proximal to BCL2 and distal to DCC. Genes, Chromosomes & Cancer 24:156-159, 1999.*

Terminology. American Society of Gene & Cell Therapy (http://www.asgt.org/about_gene_ therapy/terminology.php). 4 pages, 2010.*

Akagi et al., "Molecular Cytogenetic Delineation of the Breakpoint at 18q21.1 in Low-Grade B-Cell Lymphoma of Mucosa-Associated Lymphoid Tissue", *Genes, Chromosomes and Cancer*, 24 (4); pp. 315-321, Apr. 1999.

Dierlamm et al., "Molecular Cytogenetic Characerization of the Chromosome 11 and 18 Breakpoints in the t(11;18) (q21;q21) Associated with Malt Lymphomas" *Abstract #978*, vol. 92, No. 10, 1 page, Nov. 15, 1998.

Ott et al., "The t(11;18)(q21;q21) Chromosome Translocation Is a Frequent and Specific Aberration in Low-Grade but not High-Grade Malignant Non-Hodgkin's Lymphomas of the Mucosa-associated Lymphoid Tissue (MALT-) Type", *Cancer Research*, vol. 57, pp. 3944-3948, Sep. 1997.

Rothe et al., "The TNFR2-TRAF Signaling Complex Contains Two Novel Proteins Related to Baculoviral Inhibitor of Apoptosis Proteins", *Cell*, vol. 83, No. 7, pp. 1243-1252, Dec. 29, 1995.

PCT International Search Report, EP 99 20 1683, dated Feb. 7, 2000, 3 pages.

PCT International Search Report, EP 00/04796, dated Oct. 18, 2000, 3 pages.

Verma et al., gene therapy-promises, problems and prospects, 1997, Nature, vol. 389, pp. 239-242.

Miller et al., Targeted vectors for gene therapy, 1995, FASEB J., vol. 9, pp. 190-199.

Deonarain, Ligand-targeted receptor-mediated vectors for gene delivery, 1998, Exp. Opin. Ther. Patents, vol. 8, pp. 53-69.

Dang et al., gene therapy and translational cancer research, 1999, Clinical Cancer Research, vol. 5, pp. 471-474.

Ngo et al., Computational complexity, protein structure prediction, and the levinthal paradox, 1994, The Protein Folding Problem and Tertiary Structure Prediction, pp. 491-495.

(Continued)

*Primary Examiner*—Quang Nguyen
(74) *Attorney, Agent, or Firm*—TraskBritt

(57) ABSTRACT

Methods for determining whether a tissue sample or an analogue and/or derivative thereof comprises a cell with a chromosome (11:18) translocation associated with malignancies such as mucosa-associated lymphoid tissue (MALT) lymphomas. The invention further provides insight into a novel mechanism of transformation of primary cells. The mechanism involves expression of a fusion proteinaceous molecule comprising at least apoptosis inhibitor 2 (API2) or a functional part, derivative and/or analogue thereof fused to at least one other proteinaceous molecule. The invention also provides a novel nucleic acid sequence and proteinaceous molecule expressed from the sequence termed "MALT-lymphoma associated Translocation (MLT) protein."

7 Claims, 11 Drawing Sheets

OTHER PUBLICATIONS

Rudinger, Characteristics of amino acids as components of a peptide hormone sequence, 1976, Peptide Hormones, pp. 1-7.

Suzuki et al., API1-MALT1/MLT is involved in mucosa-associated lymphoid tissue lymphoma with t(11:18)(q21:q21), 1999, Blood, vol. 94, pp. 3270-3271.

Dierlamm et al., genetic abnormalities in marginal zone B-cell lymphoma, 2000, Hematological Oncology, vol. 18, pp. 1-13.

A Dictionary of Genetics, Fifth Edition, 1997, p. 291, Oxford University Press.

* cited by examiner

```
         gggcagcagg tttacaaagg aggaaaacga cttcttctag attttttttt cagtttcttc    60
tataaatcaa aactacctcc ctagagaaag gctagtccct tttcttcccc attcatttca   120 tt atg aac ata gta gaa aac agc ata ttc tta tca aat ttg atg aaa      167
             M   N   I   V   E   N   S   I   F   L   S   N   L   M   K agc gcc aac acg ttt gaa ctg aaa tac gac ttg tca tgt gaa ctg tac    215
          S   A   N   T   F   E   L   K   Y   D   L   S   C   E   L   Y cga atg tct acg tat tcc act ttt cct gct ggg gtc cct gtc tca gaa    263
          R   M   S   T   Y   S   T   F   P   A   G   V   P   V   S   E BIR1     agg agt ctt gct cgc gct ggt ttc tat tac act ggt gtg aat gac aag    311
          R   S   L   A   R   A   G   F   Y   Y   T   G   V   N   D   K gtc aaa tgc ttc tgt tgt ggc ctg atg ctg gat aac tgg aaa aga gga    359
          V   K   C   F   C   C   G   L   M   L   D   N   W   K   R   G gac agt cct act gaa aag cat aaa aag ttg tat cct agc tgc aga ttc    407
          D   S   P   T   E   K   H   K   K   L   Y   P   S   C   R   F gtt cag agt cta aat tcc gtt aac aac ttg gaa gct acc tct cag cct    455
          V   Q   S   L   N   S   V   N   N   L   E   A   T   S   Q   P act ttt cct tct tca gta aca aat tcc aca cac tca tta ctt ccg ggt    503
          T   F   P   S   S   V   T   N   S   T   H   S   L   L   P   G aca gaa aac agt gga tat ttc cgt ggc tct tat tca aac tct cca tca    551
          T   E   N   S   G   Y   F   R   G   S   Y   S   N   S   P   S aat cct gta aac tcc aga gca aat caa gat ttt tct gcc ttg atg aga    599
          N   P   V   N   S   R   A   N   Q   D   F   S   A   L   M   R agt tcc tac cac tgt gca atg aat aac gaa aat gcc aga tta ctt act    647
          S   S   Y   H   C   A   M   N   N   E   N   A   R   L   L   T ttt cag aca tgg cca ttg act ttt ctg tcg cca aca gat ctg gca aaa    695
          F   Q   T   W   P   L   T   F   L   S   P   T   D   L   A   K BIR2     gca ggc ttt tac tac ata gga cct gga gac aga gtg gct tgc ttt gcc    743
          A   G   F   Y   Y   I   G   P   G   D   R   V   A   C   F   A tgt ggt gga aaa ttg agc aat tgg gaa ccg aag gat aat gct atg tca    791
          C   G   G   K   L   S   N   W   E   P   K   D   N   A   M   S gaa cac ctg aga cat ttt ccc aaa tgc cca ttt ata gaa aat cag ctt    839
          E   H   L   R   H   F   P   K   C   P   F   I   E   N   Q   L
```

FIG. 5A

```
        caa gac act tca aga tac aca gtt tct aat ctg agc atg cag aca cat    887
         Q   D   T   S   R   Y   T   V   S   N   L   S   M   Q   T   H gca gcc cgc ttt aaa aca ttc ttt aac tgg ccc tct agt gtt cta gtt    935
         A   A   R   F   K   T   F   F   N   W   P   S   S   V   L   V aat cct gag cag ctt gca agt gcg ggt ttt tat tat gtg ggt aac agt    983
         N   P   E   Q   L   A   S   A   G   F   Y   Y   V   G   N   S
BIR3
        gat gat gtc aaa tgc ttt tgc tgt gat ggt gga ctc agg tgt tgg gaa    1031
         D   D   V   K   C   F   C   C   D   G   G   L   R   C   W   E tct gga gat gat cca tgg gtt caa cat gcc aag tgg ttt cca agg tgt    1079
         S   G   D   D   P   W   V   Q   H   A   K   W   F   P   R   C gag tac ttg ata aga att aaa gga cag gag ttc atc cgt caa gtt caa    1127
         E   Y   L   I   R   I   K   G   Q   E   F   I   R   Q   V   Q gcc agt tac cct cat cta ctt gaa cag ctg cta tcc aca tca gac agc    1175
         A   S   Y   P   H   L   L   E   Q   L   L   S   T   S   D   S cca gga gat gaa aat gca gag tca tca att atc cat ttt gaa cct gga    1223
         P   G   D   E   N   A   E   S   S   I   I   H   F   E   P   G gaa gac cat tca gaa gat gca atc atg atg aat act cct gtg att aat    1271
         E   D   H   S   E   D   A   I   M   M   N   T   P   V   I   N gct gcc gtg gaa atg ggc ttt agt aga agc ctg gta aaa cag aca gtt    1319
         A   A   V   E   M   G   F   S   R   S   L   V   K   Q   T   V cag aga aaa atc cta gca act gga gag aat tat aga cta gtc aat gat    1367
         Q   R   K   I   L   A   T   G   E   N   Y   R   L   V   N   D ctt gtg tta gac tta ctc aat gca gaa gat gaa ata agg gaa gag gag    1415
         L   V   L   D   L   L   N   A   E   D   E   I   R   E   E   E aga gaa aga gca act gag gaa aaa gaa tca aga ata aag att act gta    1463
         R   E   R   A   T   E   E   K   E   S   R   I   K   I   T   V aac cca gag tca aag gca gtc ttg gct gga cag ttt gtg aaa ctg tgt    1511
         N   P   E   S   K   A   V   L   A   G   Q   F   V   K   L   C tgc cgg gca act gga cat cct ttt gtt caa tat cag tgg ttc aaa atg    1559
         C   R   A   T   G   H   P   F   V   Q   Y   Q   W   F   K   M
Ig-1 C2
        aat aaa gag att cca aat gga aat aca tca gag ctt att ttt aat gca    1607
         N   K   E   I   P   N   G   N   T   S   E   L   I   F   N   A
```

FIG. 5B

```
        gtg cat gta aaa gat gca ggc ttt tat gtc tgt cga gtt aat aac aat   1655
         V   H   V   K   D   A   G   F   Y   V   C   R   V   N   N   N ttc acc ttt gaa ttc agc cag tgg tca cag ctg gat gtt tgc gac atc   1703
         F   T   F   E   F   S   Q   W   S   Q   L   D   V   C   D   I cca gag agc ttc cag aga agt gtt gat ggc gtc tct gaa tcc aag ttg   1751
         P   E   S   F   Q   R   S   V   D   G   V   S   E   S   K   L
Ig-1 C2
        caa atc tgt gtt gaa cca act tcc caa aag ctg atg cca ggc agc aca   1799
         Q   I   C   V   E   P   T   S   Q   K   L   M   P   G   S   T ttg gtt tta cag tgt gtt gct gtt gga agc cct att cct cac tac cag   1847
         L   V   L   Q   C   V   A   V   G   S   P   I   P   H   Y   Q tgg ttc aaa aat gaa tta cca tta aca cat gag acc aaa aag cta tac   1895
         W   F   K   N   E   L   P   L   T   H   E   T   K   K   L   Y atg gtg cct tat gtg gat ttg gaa cac caa gga acc tac tgg tgt cat   1943
         M   V   P   Y   V   D   L   E   H   Q   G   T   Y   W   C   H gta tat aat gat cga gac agt caa gat agc aag aag gta gaa atc atc   1991
         V   Y   N   D   R   D   S   Q   D   S   K   K   V   E   I   I ata gga aga aca gat gag gca gtg gag tgc act gaa gat gaa tta aat   2039
         I   G   R   T   D   E   A   V   E   C   T   E   D   E   L   N aat ctt ggt cat cct gat aat aaa gag caa aca act gac cag cct ttg   2087
         N   L   G   H   P   D   N   K   E   Q   T   T   D   Q   P   L gcg aag gac aag gtt gcc ctt ttg ata gga aat atg aat tac cgg gag   2135
         A   K   D   K   V   A   L   L   I   G   N   M   N   Y   R   E cac ccc aag ctc aaa gct cct ttg gtg gat gtg tac gaa ttg act aac   2183
         H   P   K   L   K   A   P   L   V   D   V   Y   E   L   T   N tta ctg aga cag ctg gac ttc aaa gtg gtt tca ctg ttg gat ctt act   2231
         L   L   R   Q   L   D   F   K   V   V   S   L   L   D   L   T gaa tat gag atg cgt aat gct gtg gat gag ttt tta ctc ctt tta gac   2279
         E   Y   E   M   R   N   A   V   D   E   F   L   L   L   L   D aag gga gta tat ggg tta tta tat tat gca gga cat ggt tat gaa aat   2327
         K   G   V   Y   G   L   L   Y   Y   A   G   H   G   Y   E   N ttt ggg aac agc ttc atg gtc ccc gtt gat gct cca aat cca tat agg   2375
         F   G   N   S   F   M   V   P   V   D   A   P   N   P   Y   R
```

FIG. 5C

```
tct gaa aat tgt ctg tgt gta caa aat ata ctg aaa ttg atg caa gaa   2423
 S   E   N   C   L   C   V   Q   N   I   L   K   L   M   Q   E aaa gaa act gga ctt aat gtg ttc tta ttg gat atg tgt agg aaa aga   2471
 K   E   T   G   L   N   V   F   L   L   D   M   C   R   K   R aat gac tac gat gat acc att cca atc ttg gat gca cta aaa gtc acc   2519
 N   D   Y   D   D   T   I   P   I   L   D   A   L   K   V   T gcc aat att gtg ttt gga tat gcc acg tgt caa gga gca gaa gct ttt   2567
 A   N   I   V   F   G   Y   A   T   C   Q   G   A   E   A   F gaa atc cag cat tct gga ttg gca aat gga atc ttt atg aaa ttt tta   2615
 E   I   Q   H   S   G   L   A   N   G   I   F   M   K   F   L aaa gac aga tta tta gaa gat aag aaa atc act gtg tta ctg gat gaa   2663
 K   D   R   L   L   E   D   K   K   I   T   V   L   L   D   E gtt gca gaa gat atg ggt aag tgt cac ctt acc aaa ggc aaa cag gct   2711
 V   A   E   D   M   G   K   C   H   L   T   K   G   K   Q   A cta gag att cga agt agt tta tct gag aag aga gca ctt act gat cca   2759
 L   E   I   R   S   S   L   S   E   K   R   A   L   T   D   P ata cag gga aca gaa tat tct gct gaa tct ctt gtg cgg aat cta cag   2807
 I   Q   G   T   E   Y   S   A   E   S   L   V   R   N   L   Q tgg gcc aag gct cat gaa ctt cca gaa agt atg tgt ctt aag ttt gac   2855
 W   A   K   A   H   E   L   P   E   S   M   C   L   K   F   D tgt ggt gtt cag att caa tta gga ttt gca gct gag ttt tcc aat gtc   2903
 C   G   V   Q   I   Q   L   G   F   A   A   E   F   S   N   V atg atc atc tat aca agt ata gtt tac aaa cca ccg gag ata ata atg   2951
 M   I   I   Y   T   S   I   V   Y   K   P   P   E   I   I   M tgt gat gcc tac gtt act gat ttt cca ctt gat cta gat att gat cca   2999
 C   D   A   Y   V   T   D   F   P   L   D   L   D   I   D   P aaa gat gca aat aaa ggc aca cct gaa gaa act ggc agc tac ttg gta   3047
 K   D   A   N   K   G   T   P   E   E   T   G   S   Y   L   V tca aag gat ctt ccc aag cat tgc ctc tat acc aga ctc agt tca ctg   3095
 S   K   D   L   P   K   H   C   L   Y   T   R   L   S   S   L caa aaa tta aag gaa cat cta gtc ttc aca gta tgt tta tca tat cag   3143
 Q   K   L   K   E   H   L   V   F   T   V   C   L   S   Y   Q
```

VDJ4

FIG. 5D

```
tac tca gga ttg gaa gat act gta gag gac aag cag gaa gtg aat gtt    3191
 Y   S   G   L   E   D   T   V   E   D   K   Q   E   V   N   V ggg aaa cct ctc att gct aaa tta gac atg cat cga ggt ttg gga agg    3239
 G   K   P   L   I   A   K   L   D   M   H   R   G   L   G   R aag act tgc ttt caa act tgt ctt atg tct aat ggt cct tac cag agt    3287
 K   T   C   F   Q   T   C   L   M   S   N   G   P   Y   Q   S tct gca gcc acc tca gga gga gca ggg cat tat cac tca ttg caa gac    3335
 S   A   A   T   S   G   G   A   G   H   Y   H   S   L   Q   D cca ttc cat ggt gtt tac cat tca cat cct ggt aat cca agt aat gtt    3383
 P   F   H   G   V   Y   H   S   H   P   G   N   P   S   N   V aca cca gca gat agc tgt cat tgc agc cgg act cca gat gca ttt att    3431
 T   P   A   D   S   C   H   C   S   R   T   P   D   A   F   I tca agt ttc gct cac cat gct tca tgt cat ttt agt aga agt aat gtg    3479
 S   S   F   A   H   H   A   S   C   H   F   S   R   S   N   V cca gta gag aca act gat gaa ata cca ttt agt ttc tct gac agg ctc    3527
 P   V   E   T   T   D   E   I   P   F   S   F   S   D   R   L aga att tct gaa aaa tga cctccttgtt tttgaaagtt agcataattt          3575
 R   I   S   E   K tagatgcctg tgaaatagta ctgcacttac ataaagtgag acattgtgaa aaggcaaatt 3635 tgtatatgta gagaaagaat agtagtaact gtttcatagc aaacttcagg actttgagat 3695 gttgaaatta cattatttaa ttacagactt cctctttct                       3734
```

FIG. 5E

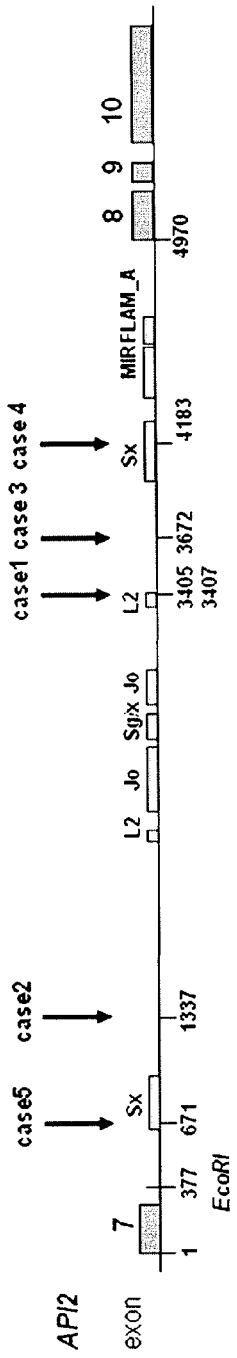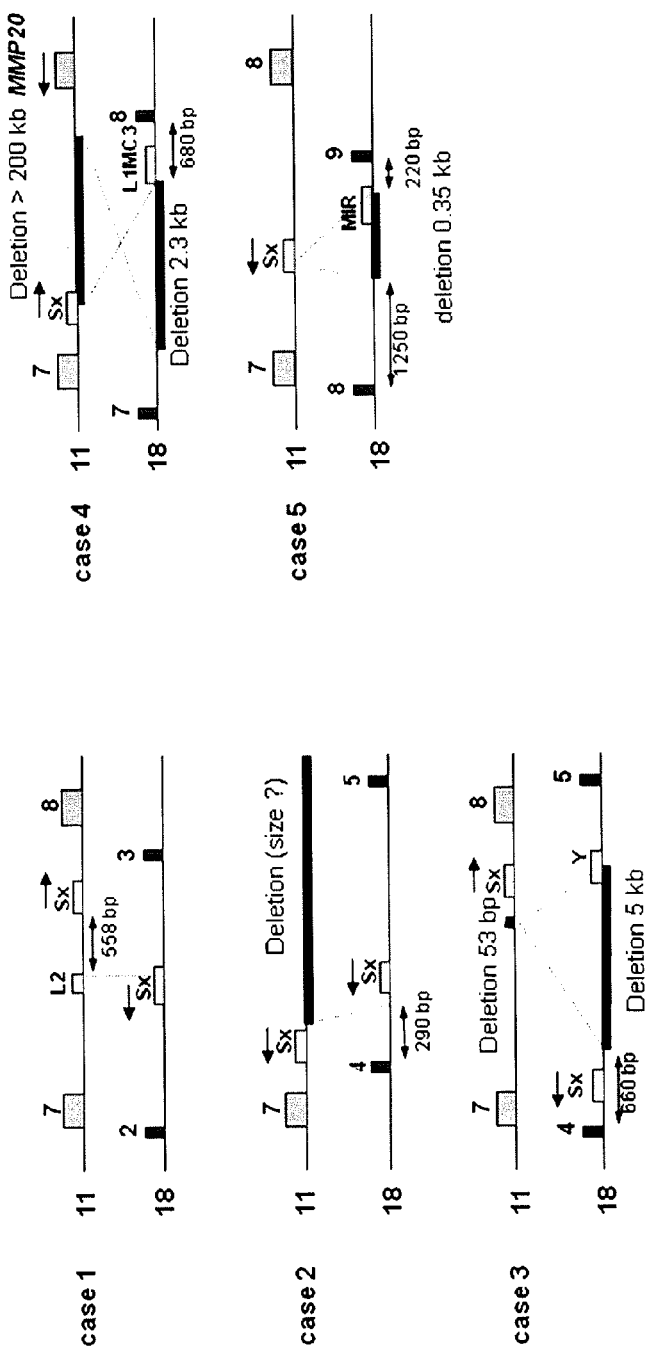
FIG. 7A
FIG. 7B

SEQUENCE LISTING

<160> NUMBER OF SEQ ID NOS: 60

<210> SEQ ID NO 1
<211> LENGTH: 43
<212> TYPE: DNA
<213> ORGANISM: Artificial Sequence
<220> FEATURE:
<223> OTHER INFORMATION: Primer R2T8

<400> SEQUENCE: 1
ccagtgagca gagtgacgag gactcgagct caagcttttt ttt          43

<210> SEQ ID NO 2
<211> LENGTH: 20
<212> TYPE: DNA
<213> ORGANISM: Artificial Sequence
<220> FEATURE:
<223> OTHER INFORMATION: Primer MLTr1

<400> SEQUENCE: 2
ccttctgcaa cttcatccag                                    20

<210> SEQ ID NO 3
<211> LENGTH: 20
<212> TYPE: DNA
<213> ORGANISM: Artificial Sequence
<220> FEATURE:
<223> OTHER INFORMATION: Primer MLTr2

<400> SEQUENCE: 3
atggatttgg agcatcaacg                                    20

<210> SEQ ID NO 4
<211> LENGTH: 18
<212> TYPE: DNA
<213> ORGANISM: Artificial Sequence
<220> FEATURE:
<223> OTHER INFORMATION: Primer R2F1

<400> SEQUENCE: 4
ccagtgagca gagtgacg                                      18

<210> SEQ ID NO 5
<211> LENGTH: 18
<212> TYPE: DNA
<213> ORGANISM: Artificial Sequence
<220> FEATURE:
<223> OTHER INFORMATION: Primer R2F2

<400> SEQUENCE: 5
gaggactcga gctcaagc                                      18

<210> SEQ ID NO 6
<211> LENGTH: 20
<212> TYPE: DNA

<213> ORGANISM: Artificial Sequence
<220> FEATURE:
<223> OTHER INFORMATION: Primer APIf1

<400> SEQUENCE: 6
ccaagtggtt tccaaggtgt                                              20

<210> SEQ ID NO 7
<211> LENGTH: 3734
<212> TYPE: DNA
<213> ORGANISM: Homo sapiens
<220> FEATURE:
<221> NAME/KEY: CDS
<222> LOCATION: (123)..(3545)
<223> OTHER INFORMATION:
<220> FEATURE:
<221> NAME/KEY: misc_feature
<222> LOCATION: (1)..(1446)
<223> OTHER INFORMATION: API2 cDNA sequence
<220> FEATURE:
<221> NAME/KEY: misc_feature
<222> LOCATION: (1447)..(2059)
<223> OTHER INFORMATION: MLT

<400> SEQUENCE: 7

```
gggcagcagg tttacaaagg aggaaaacga cttcttctag attttttttt cagtttcttc      60
tataaatcaa aactacctcc ctagagaaag gctagtccct tttcttcccc attcatttca     120 tt atg aac ata gta gaa aac agc ata ttc tta tca aat ttg atg aaa        167
   Met Asn Ile Val Glu Asn Ser Ile Phe Leu Ser Asn Leu Met Lys
   1               5                   10                  15 agc gcc aac acg ttt gaa ctg aaa tac gac ttg tca tgt gaa ctg tac       215
Ser Ala Asn Thr Phe Glu Leu Lys Tyr Asp Leu Ser Cys Glu Leu Tyr
                20                  25                  30 cga atg tct acg tat tcc act ttt cct gct ggg gtc cct gtc tca gaa       263
Arg Met Ser Thr Tyr Ser Thr Phe Pro Ala Gly Val Pro Val Ser Glu
            35                  40                  45 agg agt ctt gct cgc gct ggt ttc tat tac act ggt gtg aat gac aag       311
Arg Ser Leu Ala Arg Ala Gly Phe Tyr Tyr Thr Gly Val Asn Asp Lys
        50                  55                  60 gtc aaa tgc ttc tgt tgt ggc ctg atg ctg gat aac tgg aaa aga gga       359
Val Lys Cys Phe Cys Cys Gly Leu Met Leu Asp Asn Trp Lys Arg Gly
    65                  70                  75 gac agt cct act gaa aag cat aaa aag ttg tat cct agc tgc aga ttc       407
Asp Ser Pro Thr Glu Lys His Lys Lys Leu Tyr Pro Ser Cys Arg Phe
80                  85                  90                  95 gtt cag agt cta aat tcc gtt aac aac ttg gaa gct acc tct cag cct       455
Val Gln Ser Leu Asn Ser Val Asn Asn Leu Glu Ala Thr Ser Gln Pro
                100                 105                 110 act ttt cct tct tca gta aca aat tcc aca cac tca tta ctt ccg ggt       503
Thr Phe Pro Ser Ser Val Thr Asn Ser Thr His Ser Leu Leu Pro Gly
            115                 120                 125 aca gaa aac agt gga tat ttc cgt ggc tct tat tca aac tct cca tca       551
Thr Glu Asn Ser Gly Tyr Phe Arg Gly Ser Tyr Ser Asn Ser Pro Ser
        130                 135                 140 aat cct gta aac tcc aga gca aat caa gat ttt tct gcc ttg atg aga       599
Asn Pro Val Asn Ser Arg Ala Asn Gln Asp Phe Ser Ala Leu Met Arg
    145                 150                 155 agt tcc tac cac tgt gca atg aat aac gaa aat gcc aga tta ctt act       647
Ser Ser Tyr His Cys Ala Met Asn Asn Glu Asn Ala Arg Leu Leu Thr
160                 165                 170                 175 ttt cag aca tgg cca ttg act ttt ctg tcg cca aca gat ctg gca aaa       695
Phe Gln Thr Trp Pro Leu Thr Phe Leu Ser Pro Thr Asp Leu Ala Lys
                180                 185                 190
```

| | | |
|---|---|---|
| gca ggc ttt tac tac ata gga cct gga gac aga gtg gct tgc ttt gcc<br>Ala Gly Phe Tyr Tyr Ile Gly Pro Gly Asp Arg Val Ala Cys Phe Ala<br>            195                        200                      205 | | 743 |
| tgt ggt gga aaa ttg agc aat tgg gaa ccg aag gat aat gct atg tca<br>Cys Gly Gly Lys Leu Ser Asn Trp Glu Pro Lys Asp Asn Ala Met Ser<br>            210                        215                      220 | | 791 |
| gaa cac ctg aga cat ttt ccc aaa tgc cca ttt ata gaa aat cag ctt<br>Glu His Leu Arg His Phe Pro Lys Cys Pro Phe Ile Glu Asn Gln Leu<br>225                        230                      235 | | 839 |
| caa gac act tca aga tac aca gtt tct aat ctg agc atg cag aca cat<br>Gln Asp Thr Ser Arg Tyr Thr Val Ser Asn Leu Ser Met Gln Thr His<br>240                        245                    250                    255 | | 887 |
| gca gcc cgc ttt aaa aca ttc ttt aac tgg ccc tct agt gtt cta gtt<br>Ala Ala Arg Phe Lys Thr Phe Phe Asn Trp Pro Ser Ser Val Leu Val<br>                    260                        265                      270 | | 935 |
| aat cct gag cag ctt gca agt gcg ggt ttt tat tat gtg ggt aac agt<br>Asn Pro Glu Gln Leu Ala Ser Ala Gly Phe Tyr Tyr Val Gly Asn Ser<br>            275                        280                      285 | | 983 |
| gat gat gtc aaa tgc ttt tgc tgt gat ggt gga ctc agg tgt tgg gaa<br>Asp Asp Val Lys Cys Phe Cys Cys Asp Gly Gly Leu Arg Cys Trp Glu<br>                    290                        295                      300 | | 1031 |
| tct gga gat gat cca tgg gtt caa cat gcc aag tgg ttt cca agg tgt<br>Ser Gly Asp Asp Pro Trp Val Gln His Ala Lys Trp Phe Pro Arg Cys<br>            305                        310                      315 | | 1079 |
| gag tac ttg ata aga att aaa gga cag gag ttc atc cgt caa gtt caa<br>Glu Tyr Leu Ile Arg Ile Lys Gly Gln Glu Phe Ile Arg Gln Val Gln<br>320                        325                    330                    335 | | 1127 |
| gcc agt tac cct cat cta ctt gaa cag ctg cta tcc aca tca gac agc<br>Ala Ser Tyr Pro His Leu Leu Glu Gln Leu Leu Ser Thr Ser Asp Ser<br>                    340                        345                      350 | | 1175 |
| cca gga gat gaa aat gca gag tca tca att atc cat ttt gaa cct gga<br>Pro Gly Asp Glu Asn Ala Glu Ser Ser Ile Ile His Phe Glu Pro Gly<br>            355                        360                      365 | | 1223 |
| gaa gac cat tca gaa gat gca atc atg atg aat act cct gtg att aat<br>Glu Asp His Ser Glu Asp Ala Ile Met Met Asn Thr Pro Val Ile Asn<br>                    370                        375                      380 | | 1271 |
| gct gcc gtg gaa atg ggc ttt agt aga agc ctg gta aaa cag aca gtt<br>Ala Ala Val Glu Met Gly Phe Ser Arg Ser Leu Val Lys Gln Thr Val<br>385                        390                    395 | | 1319 |
| cag aga aaa atc cta gca act gga gag aat tat aga cta gtc aat gat<br>Gln Arg Lys Ile Leu Ala Thr Gly Glu Asn Tyr Arg Leu Val Asn Asp<br>400                        405                    410                    415 | | 1367 |
| ctt gtg tta gac tta ctc aat gca gaa gat gaa ata agg gaa gag gag<br>Leu Val Leu Asp Leu Leu Asn Ala Glu Asp Glu Ile Arg Glu Glu Glu<br>                    420                        425                      430 | | 1415 |
| aga gaa aga gca act gag gaa aaa gaa tca aga ata aag att act gta<br>Arg Glu Arg Ala Thr Glu Glu Lys Glu Ser Arg Ile Lys Ile Thr Val<br>                      435                        440                    445 | | 1463 |
| aac cca gag tca aag gca gtc ttg gct gga cag ttt gtg aaa ctg tgt<br>Asn Pro Glu Ser Lys Ala Val Leu Ala Gly Gln Phe Val Lys Leu Cys<br>450                        455                    460 | | 1511 |
| tgc cgg gca act gga cat cct ttt gtt caa tat cag tgg ttc aaa atg<br>Cys Arg Ala Thr Gly His Pro Phe Val Gln Tyr Gln Trp Phe Lys Met<br>465                        470                    475 | | 1559 |
| aat aaa gag att cca aat gga aat aca tca gag ctt att ttt aat gca<br>Asn Lys Glu Ile Pro Asn Gly Asn Thr Ser Glu Leu Ile Phe Asn Ala<br>480                        485                    490                    495 | | 1607 |
| gtg cat gta aaa gat gca ggc ttt tat gtc tgt cga gtt aat aac aat<br>Val His Val Lys Asp Ala Gly Phe Tyr Val Cys Arg Val Asn Asn Asn | | 1655 |

```
                 500             505             510
ttc acc ttt gaa ttc agc cag tgg tca cag ctg gat gtt tgc gac atc      1703
Phe Thr Phe Glu Phe Ser Gln Trp Ser Gln Leu Asp Val Cys Asp Ile
            515             520             525 cca gag agc ttc cag aga agt gtt gat ggc gtc tct gaa tcc aag ttg      1751
Pro Glu Ser Phe Gln Arg Ser Val Asp Gly Val Ser Glu Ser Lys Leu
            530             535             540 caa atc tgt gtt gaa cca act tcc caa aag ctg atg cca ggc agc aca      1799
Gln Ile Cys Val Glu Pro Thr Ser Gln Lys Leu Met Pro Gly Ser Thr
        545             550             555 ttg gtt tta cag tgt gtt gct gtt gga agc cct att cct cac tac cag      1847
Leu Val Leu Gln Cys Val Ala Val Gly Ser Pro Ile Pro His Tyr Gln
560             565             570             575 tgg ttc aaa aat gaa tta cca tta aca cat gag acc aaa aag cta tac      1895
Trp Phe Lys Asn Glu Leu Pro Leu Thr His Glu Thr Lys Lys Leu Tyr
                580             585             590 atg gtg cct tat gtg gat ttg gaa cac caa gga acc tac tgg tgt cat      1943
Met Val Pro Tyr Val Asp Leu Glu His Gln Gly Thr Tyr Trp Cys His
            595             600             605 gta tat aat gat cga gac agt caa gat agc aag aag gta gaa atc atc      1991
Val Tyr Asn Asp Arg Asp Ser Gln Asp Ser Lys Lys Val Glu Ile Ile
        610             615             620 ata gga aga aca gat gag gca gtg gag tgc act gaa gat gaa tta aat      2039
Ile Gly Arg Thr Asp Glu Ala Val Glu Cys Thr Glu Asp Glu Leu Asn
625             630             635 aat ctt ggt cat cct gat aat aaa gag caa aca act gac cag cct ttg      2087
Asn Leu Gly His Pro Asp Asn Lys Glu Gln Thr Thr Asp Gln Pro Leu
640             645             650             655 gcg aag gac aag gtt gcc ctt ttg ata gga aat atg aat tac cgg gag      2135
Ala Lys Asp Lys Val Ala Leu Leu Ile Gly Asn Met Asn Tyr Arg Glu
                660             665             670 cac ccc aag ctc aaa gct cct ttg gtg gat gtg tac gaa ttg act aac      2183
His Pro Lys Leu Lys Ala Pro Leu Val Asp Val Tyr Glu Leu Thr Asn
            675             680             685 tta ctg aga cag ctg gac ttc aaa gtg gtt tca ctg ttg gat ctt act      2231
Leu Leu Arg Gln Leu Asp Phe Lys Val Val Ser Leu Leu Asp Leu Thr
        690             695             700 gaa tat gag atg cgt aat gct gtg gat gag ttt tta ctc ctt tta gac      2279
Glu Tyr Glu Met Arg Asn Ala Val Asp Glu Phe Leu Leu Leu Leu Asp
705             710             715 aag gga gta tat ggg tta tta tat tat gca gga cat ggt tat gaa aat      2327
Lys Gly Val Tyr Gly Leu Leu Tyr Tyr Ala Gly His Gly Tyr Glu Asn
720             725             730             735 ttt ggg aac agc ttc atg gtc ccc gtt gat gct cca aat cca tat agg      2375
Phe Gly Asn Ser Phe Met Val Pro Val Asp Ala Pro Asn Pro Tyr Arg
                740             745             750 tct gaa aat tgt ctg tgt gta caa aat ata ctg aaa ttg atg caa gaa      2423
Ser Glu Asn Cys Leu Cys Val Gln Asn Ile Leu Lys Leu Met Gln Glu
            755             760             765 aaa gaa act gga ctt aat gtg ttc tta ttg gat atg tgt agg aaa aga      2471
Lys Glu Thr Gly Leu Asn Val Phe Leu Leu Asp Met Cys Arg Lys Arg
        770             775             780 aat gac tac gat gat acc att cca atc ttg gat gca cta aaa gtc acc      2519
Asn Asp Tyr Asp Asp Thr Ile Pro Ile Leu Asp Ala Leu Lys Val Thr
785             790             795 gcc aat att gtg ttt gga tat gcc acg tgt caa gga gca gaa gct ttt      2567
Ala Asn Ile Val Phe Gly Tyr Ala Thr Cys Gln Gly Ala Glu Ala Phe
800             805             810             815 gaa atc cag cat tct gga ttg gca aat gga atc ttt atg aaa ttt tta      2615
```

```
                                                           -continued

Glu Ile Gln His Ser Gly Leu Ala Asn Gly Ile Phe Met Lys Phe Leu
            820                 825                 830 aaa gac aga tta tta gaa gat aag aaa atc act gtg tta ctg gat gaa    2663
Lys Asp Arg Leu Leu Glu Asp Lys Lys Ile Thr Val Leu Leu Asp Glu
        835                 840                 845 gtt gca gaa gat atg ggt aag tgt cac ctt acc aaa ggc aaa cag gct    2711
Val Ala Glu Asp Met Gly Lys Cys His Leu Thr Lys Gly Lys Gln Ala
    850                 855                 860 cta gag att cga agt agt tta tct gag aag aga gca ctt act gat cca    2759
Leu Glu Ile Arg Ser Ser Leu Ser Glu Lys Arg Ala Leu Thr Asp Pro
865                 870                 875 ata cag gga aca gaa tat tct gct gaa tct ctt gtg cgg aat cta cag    2807
Ile Gln Gly Thr Glu Tyr Ser Ala Glu Ser Leu Val Arg Asn Leu Gln
        880                 885                 890                 895 tgg gcc aag gct cat gaa ctt cca gaa agt atg tgt ctt aag ttt gac    2855
Trp Ala Lys Ala His Glu Leu Pro Glu Ser Met Cys Leu Lys Phe Asp
                900                 905                 910 tgt ggt gtt cag att caa tta gga ttt gca gct gag ttt tcc aat gtc    2903
Cys Gly Val Gln Ile Gln Leu Gly Phe Ala Ala Glu Phe Ser Asn Val
            915                 920                 925 atg atc atc tat aca agt ata gtt tac aaa cca ccg gag ata ata atg    2951
Met Ile Ile Tyr Thr Ser Ile Val Tyr Lys Pro Pro Glu Ile Ile Met
        930                 935                 940 tgt gat gcc tac gtt act gat ttt cca ctt gat cta gat att gat cca    2999
Cys Asp Ala Tyr Val Thr Asp Phe Pro Leu Asp Leu Asp Ile Asp Pro
945                 950                 955 aaa gat gca aat aaa ggc aca cct gaa gaa act ggc agc tac ttg gta    3047
Lys Asp Ala Asn Lys Gly Thr Pro Glu Glu Thr Gly Ser Tyr Leu Val
960                 965                 970                 975 tca aag gat ctt ccc aag cat tgc ctc tat acc aga ctc agt tca ctg    3095
Ser Lys Asp Leu Pro Lys His Cys Leu Tyr Thr Arg Leu Ser Ser Leu
                980                 985                 990 caa aaa tta aag gaa cat cta gtc ttc aca gta tgt tta tca tat cag    3143
Gln Lys Leu Lys Glu His Leu Val Phe Thr Val Cys Leu Ser Tyr Gln
            995                 1000                1005 tac tca gga ttg gaa gat act gta gag gac aag cag gaa gtg aat        3188
Tyr Ser Gly Leu Glu Asp Thr Val Glu Asp Lys Gln Glu Val Asn
        1010                1015                1020 gtt ggg aaa cct ctc att gct aaa tta gac atg cat cga ggt ttg        3233
Val Gly Lys Pro Leu Ile Ala Lys Leu Asp Met His Arg Gly Leu
    1025                1030                1035 gga agg aag act tgc ttt caa act tgt ctt atg tct aat ggt cct        3278
Gly Arg Lys Thr Cys Phe Gln Thr Cys Leu Met Ser Asn Gly Pro
    1040                1045                1050 tac cag agt tct gca gcc acc tca gga gga gca ggg cat tat cac        3323
Tyr Gln Ser Ser Ala Ala Thr Ser Gly Gly Ala Gly His Tyr His
    1055                1060                1065 tca ttg caa gac cca ttc cat ggt gtt tac cat tca cat cct ggt        3368
Ser Leu Gln Asp Pro Phe His Gly Val Tyr His Ser His Pro Gly
    1070                1075                1080 aat cca agt aat gtt aca cca gca gat agc tgt cat tgc agc cgg        3413
Asn Pro Ser Asn Val Thr Pro Ala Asp Ser Cys His Cys Ser Arg
    1085                1090                1095 act cca gat gca ttt att tca agt ttc gct cac cat gct tca tgt        3458
Thr Pro Asp Ala Phe Ile Ser Ser Phe Ala His His Ala Ser Cys
    1100                1105                1110 cat ttt agt aga agt aat gtg cca gta gag aca act gat gaa ata        3503
His Phe Ser Arg Ser Asn Val Pro Val Glu Thr Thr Asp Glu Ile
    1115                1120                1125
```

-continued

```
cca ttt agt  ttc tct gac agg ctc  aga att tct gaa aaa tga                3545
Pro Phe Ser  Phe Ser Asp Arg Leu  Arg Ile Ser Glu Lys
        1130                1135                1140 cctccttgtt tttgaaagtt agcataattt tagatgcctg tgaaatagta ctgcacttac         3605
ataaagtgag acattgtgaa aaggcaaatt tgtatatgta gagaaagaat agtagtaact         3665
gtttcatagc aaacttcagg actttgagat gttgaaatta cattatttaa ttacagactt         3725
cctctttct                                                                 3734
```

<210> SEQ ID NO 8
<211> LENGTH: 1140
<212> TYPE: PRT
<213> ORGANISM: Homo sapiens
<220> FEATURE:
<221> NAME/KEY: misc_feature
<222> LOCATION: (1)..(1446)
<223> OTHER INFORMATION: API2 cDNA sequence
<220> FEATURE:
<221> NAME/KEY: misc_feature
<222> LOCATION: (1447)..(2059)
<223> OTHER INFORMATION: MLT
<400> SEQUENCE: 8

```
Met Asn Ile Val Glu Asn Ser Ile Phe Leu Ser Asn Leu Met Lys Ser
1               5                   10                  15

Ala Asn Thr Phe Glu Leu Lys Tyr Asp Leu Ser Cys Glu Leu Tyr Arg
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Tyr Thr Gly Val Asn Asp Lys Val
    50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr Asn Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140

Pro Val Asn Ser Arg Ala Asn Gln Asp Phe Ser Ala Leu Met Arg Ser
145                 150                 155                 160

Ser Tyr His Cys Ala Met Asn Asn Glu Asn Ala Arg Leu Leu Thr Phe
                165                 170                 175

Gln Thr Trp Pro Leu Thr Phe Leu Ser Pro Thr Asp Leu Ala Lys Ala
            180                 185                 190

Gly Phe Tyr Tyr Ile Gly Pro Gly Asp Arg Val Ala Cys Phe Ala Cys
        195                 200                 205

Gly Gly Lys Leu Ser Asn Trp Glu Pro Lys Asp Asn Ala Met Ser Glu
    210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
            260                 265                 270
```

-continued

```
Pro Glu Gln Leu Ala Ser Ala Gly Phe Tyr Tyr Val Gly Asn Ser Asp
        275                 280                 285

Asp Val Lys Cys Phe Cys Cys Asp Gly Gly Leu Arg Cys Trp Glu Ser
290                 295                 300

Gly Asp Asp Pro Trp Val Gln His Ala Lys Trp Phe Pro Arg Cys Glu
305                 310                 315                 320

Tyr Leu Ile Arg Ile Lys Gly Gln Glu Phe Ile Arg Gln Val Gln Ala
                325                 330                 335

Ser Tyr Pro His Leu Leu Glu Gln Leu Leu Ser Thr Ser Asp Ser Pro
                340                 345                 350

Gly Asp Glu Asn Ala Glu Ser Ile Ile His Phe Glu Pro Gly Glu
        355                 360                 365

Asp His Ser Glu Asp Ala Ile Met Met Asn Thr Pro Val Ile Asn Ala
370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Arg
            420                 425                 430

Glu Arg Ala Thr Glu Glu Lys Glu Ser Arg Ile Lys Ile Thr Val Asn
        435                 440                 445

Pro Glu Ser Lys Ala Val Leu Ala Gly Gln Phe Val Lys Leu Cys Cys
        450                 455                 460

Arg Ala Thr Gly His Pro Phe Val Gln Tyr Gln Trp Phe Lys Met Asn
465                 470                 475                 480

Lys Glu Ile Pro Asn Gly Asn Thr Ser Glu Leu Ile Phe Asn Ala Val
                485                 490                 495

His Val Lys Asp Ala Gly Phe Tyr Val Cys Arg Val Asn Asn Asn Phe
            500                 505                 510

Thr Phe Glu Phe Ser Gln Trp Ser Gln Leu Asp Val Cys Asp Ile Pro
        515                 520                 525

Glu Ser Phe Gln Arg Ser Val Asp Gly Val Ser Glu Ser Lys Leu Gln
        530                 535                 540

Ile Cys Val Glu Pro Thr Ser Gln Lys Leu Met Pro Gly Ser Thr Leu
545                 550                 555                 560

Val Leu Gln Cys Val Ala Val Gly Ser Pro Ile Pro His Tyr Gln Trp
                565                 570                 575

Phe Lys Asn Glu Leu Pro Leu Thr His Glu Thr Lys Lys Leu Tyr Met
            580                 585                 590

Val Pro Tyr Val Asp Leu Glu His Gln Gly Thr Tyr Trp Cys His Val
        595                 600                 605

Tyr Asn Asp Arg Asp Ser Gln Asp Ser Lys Lys Val Glu Ile Ile Ile
610                 615                 620

Gly Arg Thr Asp Glu Ala Val Glu Cys Thr Glu Asp Glu Leu Asn Asn
625                 630                 635                 640

Leu Gly His Pro Asp Asn Lys Glu Gln Thr Thr Asp Gln Pro Leu Ala
                645                 650                 655

Lys Asp Lys Val Ala Leu Leu Ile Gly Asn Met Asn Tyr Arg Glu His
            660                 665                 670

Pro Lys Leu Lys Ala Pro Leu Val Asp Val Tyr Glu Leu Thr Asn Leu
        675                 680                 685

Leu Arg Gln Leu Asp Phe Lys Val Val Ser Leu Leu Asp Leu Thr Glu
```

-continued

```
            690                 695                 700
Tyr Glu Met Arg Asn Ala Val Asp Glu Phe Leu Leu Leu Asp Lys
705                 710                 715                 720

Gly Val Tyr Gly Leu Leu Tyr Tyr Ala Gly His Gly Tyr Glu Asn Phe
                725                 730                 735

Gly Asn Ser Phe Met Val Pro Val Asp Ala Pro Asn Pro Tyr Arg Ser
                740                 745                 750

Glu Asn Cys Leu Cys Val Gln Asn Ile Leu Lys Leu Met Gln Glu Lys
                755                 760                 765

Glu Thr Gly Leu Asn Val Phe Leu Leu Asp Met Cys Arg Lys Arg Asn
770                 775                 780

Asp Tyr Asp Asp Thr Ile Pro Ile Leu Asp Ala Leu Lys Val Thr Ala
785                 790                 795                 800

Asn Ile Val Phe Gly Tyr Ala Thr Cys Gln Gly Ala Glu Ala Phe Glu
                805                 810                 815

Ile Gln His Ser Gly Leu Ala Asn Gly Ile Phe Met Lys Phe Leu Lys
                820                 825                 830

Asp Arg Leu Leu Glu Asp Lys Lys Ile Thr Val Leu Leu Asp Glu Val
                835                 840                 845

Ala Glu Asp Met Gly Lys Cys His Leu Thr Lys Gly Lys Gln Ala Leu
850                 855                 860

Glu Ile Arg Ser Ser Leu Ser Glu Lys Arg Ala Leu Thr Asp Pro Ile
865                 870                 875                 880

Gln Gly Thr Glu Tyr Ser Ala Glu Ser Leu Val Arg Asn Leu Gln Trp
                885                 890                 895

Ala Lys Ala His Glu Leu Pro Glu Ser Met Cys Leu Lys Phe Asp Cys
                900                 905                 910

Gly Val Gln Ile Gln Leu Gly Phe Ala Ala Glu Phe Ser Asn Val Met
                915                 920                 925

Ile Ile Tyr Thr Ser Ile Val Tyr Lys Pro Pro Glu Ile Ile Met Cys
                930                 935                 940

Asp Ala Tyr Val Thr Asp Phe Pro Leu Asp Leu Asp Ile Asp Pro Lys
945                 950                 955                 960

Asp Ala Asn Lys Gly Thr Pro Glu Glu Thr Gly Ser Tyr Leu Val Ser
                965                 970                 975

Lys Asp Leu Pro Lys His Cys Leu Tyr Thr Arg Leu Ser Ser Leu Gln
                980                 985                 990

Lys Leu Lys Glu His Leu Val Phe Thr Val Cys Leu Ser Tyr Gln Tyr
                995                 1000                1005

Ser Gly Leu Glu Asp Thr Val Glu Asp Lys Gln Glu Val Asn Val
    1010                1015                1020

Gly Lys Pro Leu Ile Ala Lys Leu Asp Met His Arg Gly Leu Gly
    1025                1030                1035

Arg Lys Thr Cys Phe Gln Thr Cys Leu Met Ser Asn Gly Pro Tyr
    1040                1045                1050

Gln Ser Ser Ala Ala Thr Ser Gly Gly Ala Gly His Tyr His Ser
    1055                1060                1065

Leu Gln Asp Pro Phe His Gly Val Tyr His Ser His Pro Gly Asn
    1070                1075                1080

Pro Ser Asn Val Thr Pro Ala Asp Ser Cys His Cys Ser Arg Thr
    1085                1090                1095

Pro Asp Ala Phe Ile Ser Ser Phe Ala His Ala Ser Cys His
    1100                1105                1110
```

```
Phe Ser  Arg Ser Asn Val Pro  Val Glu Thr Thr Asp  Glu Ile Pro
    1115              1120              1125

Phe Ser  Phe Ser Asp Arg Leu  Arg Ile Ser Glu Lys
    1130              1135              1140

<210> SEQ ID NO 9
<211> LENGTH: 14
<212> TYPE: DNA
<213> ORGANISM: Homo sapiens
<220> FEATURE:
<221> NAME/KEY: exon
<222> LOCATION: (1)..(8)
<223> OTHER INFORMATION: 3' end of the exon 1 at the exon-intron
      boundary of the human MLT gene.
<220> FEATURE:
<221> NAME/KEY: Intron
<222> LOCATION: (9)..(14)
<223> OTHER INFORMATION: 5' end of the intron at the exon-intron
      boundary of the human MLT gene.

<400> SEQUENCE: 9 cgc ctc ag gtgagc                                                    14
Arg Leu
1

<210> SEQ ID NO 10
<211> LENGTH: 25
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(25)
<223> OTHER INFORMATION: 5' end of the next exon at the exon-intron
      boundary of the human MLT gene.

<400> SEQUENCE: 10
tctttctgtt gctttcag ttg cct a                                        25
                    Leu Pro
                      1

<210> SEQ ID NO 11
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
<220> FEATURE:
<221> NAME/KEY: Intron
<222> LOCATION: (8)..(13)
<223> OTHER INFORMATION: 5' end of the intron at the exon-intron
      boundary of the human MLT gene.

<400> SEQUENCE: 11 ccc cca g gtaggt                                                     13
Pro Pro
1

<210> SEQ ID NO 12
<211> LENGTH: 26
<212> TYPE: DNA
<213> ORGANISM: Homo sapiens
<220> FEATURE:
```

```
<221> NAME/KEY: Intron
<222> LOCATION: (1)..(17)
<223> OTHER INFORMATION: 3' end of the intron at the exon-intron
      boundary of the human MLT gene.
<220> FEATURE:
<221> NAME/KEY: exon
<222> LOCATION: (18)..(26)
<223> OTHER INFORMATION: 5' end of the next exon at the exon-intron
      boundary of the human MLT gene.

<400> SEQUENCE: 12
tttttttttt tttttta gga ata aag                                           26
                   Gly Ile Lys
                    1

<210> SEQ ID NO 13
<211> LENGTH: 15
<212> TYPE: DNA
<213> ORGANISM: Homo sapiens
<220> FEATURE:
<221> NAME/KEY: exon
<222> LOCATION: (1)..(9)
<223> OTHER INFORMATION: 3' end of the exon at the exon-intron boundary
      of the human MLT gene.
<220> FEATURE:
<221> NAME/KEY: Intron
<222> LOCATION: (10)..(15)
<223> OTHER INFORMATION: 5' end of the intron at the exon-intron
      boundary of the human MLT gene.

<400> SEQUENCE: 13 aat aaa gag gtaatt                                                       15
Asn Lys Glu
 1

<210> SEQ ID NO 14
<211> LENGTH: 27
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(27)
<223> OTHER INFORMATION: 5' end of the next exon at the exon-intron
      boundary of the human MLT gene.

<400> SEQUENCE: 14
tcttattgat cttcacag att cca aat                                          27
                    Ile Pro Asn
                     1

<210> SEQ ID NO 15
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
<220> FEATURE:
<221> NAME/KEY: exon
<222> LOCATION: (8)..(13)
<223> OTHER INFORMATION: 5' end of the intron at the exon-intron
      boundary of the human MLT gene.

<400> SEQUENCE: 15 ttc cag a gt  aag t                                                      13
```

```
Phe Gln  Ser Lys
1

<210> SEQ ID NO 16
<211> LENGTH: 26
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(26)
<223> OTHER INFORMATION: 5' end of the next exon at the exon-intron
      boundary of the human MLT gene.

<400> SEQUENCE: 16
ttttcttttt aatttaag gaa gtg tt                                    26
                Glu Val
                1

<210> SEQ ID NO 17
<211> LENGTH: 15
<212> TYPE: DNA
<213> ORGANISM: Homo sapiens
<220> FEATURE:
<221> NAME/KEY: exon
<222> LOCATION: (1)..(9)
<223> OTHER INFORMATION: 3' end of the exon at the exon-intron boundary
      of the human MLT gene.
<220> FEATURE:
<221> NAME/KEY: Intron
<222> LOCATION: (10)..(15)
<223> OTHER INFORMATION: 5' end of the intron at the exon-intron
      boundary of the human MLT gene.

<400> SEQUENCE: 17 cta tac atg gtagga                                                15
Leu Tyr Met
1

<210> SEQ ID NO 18
<211> LENGTH: 27
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(27)
<223> OTHER INFORMATION: 5' end of the next exon at the exon-intron
      boundary of the human MLT gene.

<400> SEQUENCE: 18
gttctaatat tgatatag gtg cct tat                                   27
                Val Pro Tyr
                1

<210> SEQ ID NO 19
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
```

```
<220> FEATURE:
<221> NAME/KEY: Intron
<222> LOCATION: (8)..(13)
<223> OTHER INFORMATION: 5' end of the intron at the exon-intron
      boundary of the human MLT gene.

<400> SEQUENCE: 19 atc ata g gtaaga                                                          13
Ile Ile
1

<210> SEQ ID NO 20
<211> LENGTH: 26
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(26)
<223> OTHER INFORMATION: 5' end of the next exon at the exon-intron
      boundary of the human MLT gene.

<400> SEQUENCE: 20
tgttttttct gaaacaag gaa gaa ca                                            26
                    Glu Glu
                     1

<210> SEQ ID NO 21
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
<220> FEATURE:
<221> NAME/KEY: Intron
<222> LOCATION: (8)..(13)
<223> OTHER INFORMATION: 5' end of the intron at the exon-intron
      boundary of the human MLT gene.

<400> SEQUENCE: 21 act gaa g gtagtg                                                          13
Thr Glu
1

<210> SEQ ID NO 22
<211> LENGTH: 26
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron
<220> FEATURE:
<221> NAME/KEY: exon
<222> LOCATION: (19)..(26)
<223> OTHER INFORMATION: 5' end of the next exon at the exon-intron
      boundary of the human MLT gene.

<400> SEQUENCE: 22
tctcttactt tgttttag atg aat ta                                            26
                    Met Asn
                     1

<210> SEQ ID NO 23
```

```
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
<220> FEATURE:
<221> NAME/KEY: Intron
<222> LOCATION: (8)..(13)
<223> OTHER INFORMATION: 5' end of the intron at the exon-intron
      boundary of the human MLT gene.

<400> SEQUENCE: 23 cat cct g gtgagt                                                          13
His Pro
1

<210> SEQ ID NO 24
<211> LENGTH: 26
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(26)
<223> OTHER INFORMATION: 5' end of the next exon at the exon-intron
      boundary of the human MLT gene.

<400> SEQUENCE: 24 tttttttatct ttgtatag ata ata aa                                           26
                    Ile Ile
                     1

<210> SEQ ID NO 25
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
<220> FEATURE:
<221> NAME/KEY: Intron
<222> LOCATION: (8)..(13)
<223> OTHER INFORMATION: 5' end of the intron at the exon-intron
      boundary of the human MLT gene.

<400> SEQUENCE: 25 cct ttg g gtgagt                                                          13
Pro Leu
1

<210> SEQ ID NO 26
<211> LENGTH: 26
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(26)
<223> OTHER INFORMATION: 5' end of the next exon at the exon-intron
      boundary of the human MLT gene.
```

```
<400> SEQUENCE: 26 tttcttttttt tttcaaag cga agg ac                                      26
                    Arg Arg
                     1

<210> SEQ ID NO 27
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
<220> FEATURE:
<221> NAME/KEY: Intron
<222> LOCATION: (8)..(13)
<223> OTHER INFORMATION: 5' end of the intron at the exon-intron
      boundary of the human MLT gene.

<400> SEQUENCE: 27 gta tat g gtaaga                                                     13
Val Tyr
 1

<210> SEQ ID NO 28
<211> LENGTH: 26
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(26)
<223> OTHER INFORMATION: 5' end of the next exon at the exon-intron
      boundary of the human MLT gene.

<400> SEQUENCE: 28 tattttcccct cttttcag ggt tat ta                                      26
                    Gly Tyr
                     1

<210> SEQ ID NO 29
<211> LENGTH: 14
<212> TYPE: DNA
<213> ORGANISM: Homo sapiens
<220> FEATURE:
<221> NAME/KEY: exon
<222> LOCATION: (1)..(8)
<223> OTHER INFORMATION: 3' end of the exon at the exon-intron boundary
      of the human MLT gene.
<220> FEATURE:
<221> NAME/KEY: Intron
<222> LOCATION: (9)..(14)
<223> OTHER INFORMATION: 5' end of the intron at the exon-intron
      boundary of the human MLT gene.

<400> SEQUENCE: 29 agg aaa ag gtaagt                                                    14
Arg Lys
 1

<210> SEQ ID NO 30
<211> LENGTH: 25
<212> TYPE: DNA
<213> ORGANISM: Homo sapiens
<220> FEATURE:
```

```
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(25)
<223> OTHER INFORMATION: 5' end of the next exon at the exon-intron
      boundary of the human MLT gene.

<400> SEQUENCE: 30
tccgcctccc ttaaatag aaa tga c                                         25
                    Lys
                     1

<210> SEQ ID NO 31
<211> LENGTH: 14
<212> TYPE: DNA
<213> ORGANISM: Homo sapiens
<220> FEATURE:
<221> NAME/KEY: exon
<222> LOCATION: (1)..(8)
<223> OTHER INFORMATION: 3' end of the exon at the exon-intron boundary
      of the human MLT gene.
<220> FEATURE:
<221> NAME/KEY: Intron
<222> LOCATION: (9)..(14)
<223> OTHER INFORMATION: 5' end of the intron at the exon-intron
      boundary of the human MLT gene.

<400> SEQUENCE: 31 tat gcc ac gtaaga                                                     14
Tyr Ala
 1

<210> SEQ ID NO 32
<211> LENGTH: 25
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(25)
<223> OTHER INFORMATION: 5' end of the next exon at the exon-intron
      boundary of the human MLT gene.

<400> SEQUENCE: 32 tcttttttcta tttttaag gtg tca a                                        25
                     Val Ser
                      1

<210> SEQ ID NO 33
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
<220> FEATURE:
<221> NAME/KEY: Intron
<222> LOCATION: (8)..(13)
<223> OTHER INFORMATION: 5' end of the intron at the exon-intron
      boundary of the human MLT gene.

<400> SEQUENCE: 33 gca gaa g gtaaaa                                                      13
```

Ala Glu
1

<210> SEQ ID NO 34
<211> LENGTH: 26
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(26)
<223> OTHER INFORMATION: 5' end of the next exon at the exon-intron
      boundary of the human MLT gene.

<400> SEQUENCE: 34
tattttcata tcttttag ata tgg gt                                    26
                    Ile Trp
                    1

<210> SEQ ID NO 35
<211> LENGTH: 13
<212> TYPE: DNA
<213> ORGANISM: Homo sapiens
<220> FEATURE:
<221> NAME/KEY: exon
<222> LOCATION: (1)..(7)
<223> OTHER INFORMATION: 3' end of the exon at the exon-intron boundary
      of the human MLT gene.
<220> FEATURE:
<221> NAME/KEY: Intron
<222> LOCATION: (8)..(13)
<223> OTHER INFORMATION: 5' end of the intron at the exon-intron
      boundary of the human MLT gene.

<400> SEQUENCE: 35 gct cat g gtacgg                                                  13
Ala His
1

<210> SEQ ID NO 36
<211> LENGTH: 26
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(26)
<223> OTHER INFORMATION: 5' end of the next exon at the exon-intron
      boundary of the human MLT gene.

<400> SEQUENCE: 36
cttattgttc tttttcag aac ttc ca                                    26
                    Asn Phe
                    1

<210> SEQ ID NO 37
<211> LENGTH: 15
<212> TYPE: DNA
<213> ORGANISM: Homo sapiens
<220> FEATURE:
<221> NAME/KEY: exon
<222> LOCATION: (1)..(9)
<223> OTHER INFORMATION: 3' end of the exon at the exon-intron boundary
      of the human MLT gene.

```
<220> FEATURE:
<221> NAME/KEY: Intron
<222> LOCATION: (10)..(15)
<223> OTHER INFORMATION: 5' end of the intron at the exon-intron
      boundary of the human MLT gene.

<400> SEQUENCE: 37 ttt cca ctt gtgagt                                                     15
Phe Pro Leu
1

<210> SEQ ID NO 38
<211> LENGTH: 27
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(27)
<223> OTHER INFORMATION: 5' end of the next exon at the exon-intron
      boundary of the human MLT gene.

<400> SEQUENCE: 38 taatttttt ttttacag gat cta gat                                         27
                   Asp Leu Asp
                   1

<210> SEQ ID NO 39
<211> LENGTH: 15
<212> TYPE: DNA
<213> ORGANISM: Homo sapiens
<220> FEATURE:
<221> NAME/KEY: exon
<222> LOCATION: (1)..(9)
<223> OTHER INFORMATION: 3' end of the exon at the exon-intron boundary
      of the human MLT gene.
<220> FEATURE:
<221> NAME/KEY: Intron
<222> LOCATION: (10)..(15)
<223> OTHER INFORMATION: 5' end of the intron at the exon-intron
      boundary of the human MLT gene.

<400> SEQUENCE: 39 aaa tta aag gttact                                                     15
Lys Leu Lys
1

<210> SEQ ID NO 40
<211> LENGTH: 27
<212> TYPE: DNA
<213> ORGANISM: Homo sapiens
<220> FEATURE:
<221> NAME/KEY: Intron
<222> LOCATION: (1)..(18)
<223> OTHER INFORMATION: 3' end of the intron at the exon-intron
      boundary of the human MLT gene.
<220> FEATURE:
<221> NAME/KEY: exon
<222> LOCATION: (19)..(27)
<223> OTHER INFORMATION: 5' end of the next exon at the exon-intron
      boundary of the human MLT gene.

<400> SEQUENCE: 40
gatttttttc cttttcag gaa cat cta                                        27
                    Glu His Leu
                    1
```

<210> SEQ ID NO 41
<211> LENGTH: 20
<212> TYPE: DNA
<213> ORGANISM: Artificial Sequence
<220> FEATURE:
<223> OTHER INFORMATION: Primer API2-1266f

<400> SEQUENCE: 41
attaatgctg ccgtggaaat                                        20

<210> SEQ ID NO 42
<211> LENGTH: 23
<212> TYPE: DNA
<213> ORGANISM: Artificial Sequence
<220> FEATURE:
<223> OTHER INFORMATION: Primer API2-1301f

<400> SEQUENCE: 42
cctggtaaaa cagacagttc aga                                    23

<210> SEQ ID NO 43
<211> LENGTH: 24
<212> TYPE: DNA
<213> ORGANISM: Artificial Sequence
<220> FEATURE:
<223> OTHER INFORMATION: Primer MLT-i2r1

<400> SEQUENCE: 43
caggtggtgg ataacgtgga gttt                                   24

<210> SEQ ID NO 44
<211> LENGTH: 24
<212> TYPE: DNA
<213> ORGANISM: Artificial Sequence
<220> FEATURE:
<223> OTHER INFORMATION: Primer MLT-i2r2

<400> SEQUENCE: 44
cacaaatctg cctggccaga gaag                                   24

<210> SEQ ID NO 45
<211> LENGTH: 24
<212> TYPE: DNA
<213> ORGANISM: Artificial Sequence
<220> FEATURE:
<223> OTHER INFORMATION: Primer MLT-984r

<400> SEQUENCE: 45 gcttttggt ctcatgtgtt aatg                                    24

<210> SEQ ID NO 46
<211> LENGTH: 20
<212> TYPE: DNA
<213> ORGANISM: Artificial Sequence
<220> FEATURE:
<223> OTHER INFORMATION: Primer MLT-929r

<400> SEQUENCE: 46
aatagggctt ccaacagcaa                                        20

<210> SEQ ID NO 47
<211> LENGTH: 24
<212> TYPE: DNA
<213> ORGANISM: Artificial Sequence
<220> FEATURE:
<223> OTHER INFORMATION: Primer MLT-1147r

<400> SEQUENCE: 47
ggatgaccaa gattatttaa ttca                                              24

<210> SEQ ID NO 48
<211> LENGTH: 21
<212> TYPE: DNA
<213> ORGANISM: Artificial Sequence
<220> FEATURE:
<223> OTHER INFORMATION: Primer MLT-1181r

<400> SEQUENCE: 48
caaaggctgg tcagttgttt g                                                 21

<210> SEQ ID NO 49
<211> LENGTH: 21
<212> TYPE: DNA
<213> ORGANISM: Artificial Sequence
<220> FEATURE:
<223> OTHER INFORMATION: Primer API2-1684r

<400> SEQUENCE: 49
aacacagctt cagcttcttg c                                                 21

<210> SEQ ID NO 50
<211> LENGTH: 25
<212> TYPE: DNA
<213> ORGANISM: Artificial Sequence
<220> FEATURE:
<223> OTHER INFORMATION: Primer API2-1546r

<400> SEQUENCE: 50
ttaataattc cggcagttag tagac                                             25

<210> SEQ ID NO 51
<211> LENGTH: 23
<212> TYPE: DNA
<213> ORGANISM: Artificial Sequence
<220> FEATURE:
<223> OTHER INFORMATION: Primer MLT-i2f1

<400> SEQUENCE: 51
ggttgagctt ggaaagacaa agg                                               23

<210> SEQ ID NO 52
<211> LENGTH: 25
<212> TYPE: DNA
<213> ORGANISM: Artificial Sequence
<220> FEATURE:
<223> OTHER INFORMATION: Primer MLT-i2f2

<400> SEQUENCE: 52
acctgatgca ctctatttta cgtgg                                             25

<210> SEQ ID NO 53
<211> LENGTH: 20
<212> TYPE: DNA
<213> ORGANISM: Artificial Sequence
<220> FEATURE:
<223> OTHER INFORMATION: Primer MLT-717f

<400> SEQUENCE: 53
gcaggctttt atgtctgtcg                                                   20

<210> SEQ ID NO 54
<211> LENGTH: 20

-continued

```
<212> TYPE: DNA
<213> ORGANISM: Artificial Sequence
<220> FEATURE:
<223> OTHER INFORMATION: Primer MLT-757f

<400> SEQUENCE: 54
ttgaattcag ccagtggtca                                              20

<210> SEQ ID NO 55
<211> LENGTH: 27
<212> TYPE: DNA
<213> ORGANISM: Artificial Sequence
<220> FEATURE:
<223> OTHER INFORMATION: Primer MLT-i8f1

<400> SEQUENCE: 55
cttttgtaaa tagccaccac taagatt                                      27

<210> SEQ ID NO 56
<211> LENGTH: 25
<212> TYPE: DNA
<213> ORGANISM: Artificial Sequence
<220> FEATURE:
<223> OTHER INFORMATION: Primer MLT-i8f2

<400> SEQUENCE: 56
ttcccacaat tcagggagta ccaaa                                        25

<210> SEQ ID NO 57
<211> LENGTH: 1448
<212> TYPE: DNA
<213> ORGANISM: Homo sapiens
<220> FEATURE:
<221> NAME/KEY: CDS
<222> LOCATION: (123)..(1448)
<223> OTHER INFORMATION:
<220> FEATURE:
<221> NAME/KEY: misc_feature
<222> LOCATION: (1)..(1446)
<223> OTHER INFORMATION: API2 cDNA sequence

<400> SEQUENCE: 57
gggcagcagg tttacaaagg aggaaaacga cttcttctag attttttttt cagtttcttc    60
tataaatcaa aactacctcc ctagagaaag gctagtccct tttcttcccc attcatttca   120 tt atg aac ata gta gaa aac agc ata ttc tta tca aat ttg atg aaa     167
   Met Asn Ile Val Glu Asn Ser Ile Phe Leu Ser Asn Leu Met Lys
   1               5                   10                  15 agc gcc aac acg ttt gaa ctg aaa tac gac ttg tca tgt gaa ctg tac   215
Ser Ala Asn Thr Phe Glu Leu Lys Tyr Asp Leu Ser Cys Glu Leu Tyr
                20                  25                  30 cga atg tct acg tat tcc act ttt cct gct ggg gtc cct gtc tca gaa   263
Arg Met Ser Thr Tyr Ser Thr Phe Pro Ala Gly Val Pro Val Ser Glu
            35                  40                  45 agg agt ctt gct cgc gct ggt ttc tat tac act ggt gtg aat gac aag   311
Arg Ser Leu Ala Arg Ala Gly Phe Tyr Tyr Thr Gly Val Asn Asp Lys
        50                  55                  60 gtc aaa tgc ttc tgt tgt ggc ctg atg ctg gat aac tgg aaa aga gga   359
Val Lys Cys Phe Cys Cys Gly Leu Met Leu Asp Asn Trp Lys Arg Gly
    65                  70                  75 gac agt cct act gaa aag cat aaa aag ttg tat cct agc tgc aga ttc   407
Asp Ser Pro Thr Glu Lys His Lys Lys Leu Tyr Pro Ser Cys Arg Phe
80                  85                  90                  95 gtt cag agt cta aat tcc gtt aac aac ttg gaa gct acc tct cag cct   455
Val Gln Ser Leu Asn Ser Val Asn Asn Leu Glu Ala Thr Ser Gln Pro
```

-continued

```
                 100                 105                 110
act ttt cct tct tca gta aca aat tcc aca cac tca tta ctt ccg ggt      503
Thr Phe Pro Ser Ser Val Thr Asn Ser Thr His Ser Leu Leu Pro Gly
            115                 120                 125 aca gaa aac agt gga tat ttc cgt ggc tct tat tca aac tct cca tca      551
Thr Glu Asn Ser Gly Tyr Phe Arg Gly Ser Tyr Ser Asn Ser Pro Ser
        130                 135                 140 aat cct gta aac tcc aga gca aat caa gat ttt tct gcc ttg atg aga      599
Asn Pro Val Asn Ser Arg Ala Asn Gln Asp Phe Ser Ala Leu Met Arg
    145                 150                 155 agt tcc tac cac tgt gca atg aat aac gaa aat gcc aga tta ctt act      647
Ser Ser Tyr His Cys Ala Met Asn Asn Glu Asn Ala Arg Leu Leu Thr
160                 165                 170                 175 ttt cag aca tgg cca ttg act ttt ctg tcg cca aca gat ctg gca aaa      695
Phe Gln Thr Trp Pro Leu Thr Phe Leu Ser Pro Thr Asp Leu Ala Lys
            180                 185                 190 gca ggc ttt tac tac ata gga cct gga gac aga gtg gct tgc ttt gcc      743
Ala Gly Phe Tyr Tyr Ile Gly Pro Gly Asp Arg Val Ala Cys Phe Ala
        195                 200                 205 tgt ggt gga aaa ttg agc aat tgg gaa ccg aag gat aat gct atg tca      791
Cys Gly Gly Lys Leu Ser Asn Trp Glu Pro Lys Asp Asn Ala Met Ser
    210                 215                 220 gaa cac ctg aga cat ttt ccc aaa tgc cca ttt ata gaa aat cag ctt      839
Glu His Leu Arg His Phe Pro Lys Cys Pro Phe Ile Glu Asn Gln Leu
225                 230                 235 caa gac act tca aga tac aca gtt tct aat ctg agc atg cag aca cat      887
Gln Asp Thr Ser Arg Tyr Thr Val Ser Asn Leu Ser Met Gln Thr His
240                 245                 250                 255 gca gcc cgc ttt aaa aca ttc ttt aac tgg ccc tct agt gtt cta gtt      935
Ala Ala Arg Phe Lys Thr Phe Phe Asn Trp Pro Ser Ser Val Leu Val
            260                 265                 270 aat cct gag cag ctt gca agt gcg ggt ttt tat tat gtg ggt aac agt      983
Asn Pro Glu Gln Leu Ala Ser Ala Gly Phe Tyr Tyr Val Gly Asn Ser
        275                 280                 285 gat gat gtc aaa tgc ttt tgc tgt gat ggt gga ctc agg tgt tgg gaa     1031
Asp Asp Val Lys Cys Phe Cys Cys Asp Gly Gly Leu Arg Cys Trp Glu
    290                 295                 300 tct gga gat gat cca tgg gtt caa cat gcc aag tgg ttt cca agg tgt     1079
Ser Gly Asp Asp Pro Trp Val Gln His Ala Lys Trp Phe Pro Arg Cys
305                 310                 315 gag tac ttg ata aga att aaa gga cag gag ttc atc cgt caa gtt caa     1127
Glu Tyr Leu Ile Arg Ile Lys Gly Gln Glu Phe Ile Arg Gln Val Gln
320                 325                 330                 335 gcc agt tac cct cat cta ctt gaa cag ctg cta tcc aca tca gac agc     1175
Ala Ser Tyr Pro His Leu Leu Glu Gln Leu Leu Ser Thr Ser Asp Ser
            340                 345                 350 cca gga gat gaa aat gca gag tca tca att atc cat ttt gaa cct gga     1223
Pro Gly Asp Glu Asn Ala Glu Ser Ser Ile Ile His Phe Glu Pro Gly
        355                 360                 365 gaa gac cat tca gaa gat gca atc atg atg aat act cct gtg att aat     1271
Glu Asp His Ser Glu Asp Ala Ile Met Met Asn Thr Pro Val Ile Asn
    370                 375                 380 gct gcc gtg gaa atg ggc ttt agt aga agc ctg gta aaa cag aca gtt     1319
Ala Ala Val Glu Met Gly Phe Ser Arg Ser Leu Val Lys Gln Thr Val
385                 390                 395 cag aga aaa atc cta gca act gga gag aat tat aga cta gtc aat gat     1367
Gln Arg Lys Ile Leu Ala Thr Gly Glu Asn Tyr Arg Leu Val Asn Asp
400                 405                 410                 415 ctt gtg tta gac tta ctc aat gca gaa gat gaa ata agg gaa gag gag     1415
```

```
Leu Val Leu Asp Leu Leu Asn Ala Glu Asp Glu Ile Arg Glu Glu Glu
            420                 425                 430 aga gaa aga gca act gag gaa aaa gaa tca aga                                    1448
Arg Glu Arg Ala Thr Glu Glu Lys Glu Ser Arg
            435                 440

<210> SEQ ID NO 58
<211> LENGTH: 442
<212> TYPE: PRT
<213> ORGANISM: Homo sapiens
<220> FEATURE:
<221> NAME/KEY: misc_feature
<222> LOCATION: (1)..(1446)
<223> OTHER INFORMATION: API2 cDNA sequence

<400> SEQUENCE: 58

Met Asn Ile Val Glu Asn Ser Ile Phe Leu Ser Asn Leu Met Lys Ser
1               5                   10                  15

Ala Asn Thr Phe Glu Leu Lys Tyr Asp Leu Ser Cys Glu Leu Tyr Arg
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Tyr Thr Gly Val Asn Asp Lys Val
    50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
            85                  90                  95

Gln Ser Leu Asn Ser Val Asn Asn Leu Glu Ala Thr Ser Gln Pro Thr
            100                 105                 110

Phe Pro Ser Ser Val Thr Asn Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140

Pro Val Asn Ser Arg Ala Asn Gln Asp Phe Ser Ala Leu Met Arg Ser
145                 150                 155                 160

Ser Tyr His Cys Ala Met Asn Asn Glu Asn Ala Arg Leu Leu Thr Phe
            165                 170                 175

Gln Thr Trp Pro Leu Thr Phe Leu Ser Pro Thr Asp Leu Ala Lys Ala
            180                 185                 190

Gly Phe Tyr Tyr Ile Gly Pro Gly Asp Arg Val Ala Cys Phe Ala Cys
        195                 200                 205

Gly Gly Lys Leu Ser Asn Trp Glu Pro Lys Asp Asn Ala Met Ser Glu
    210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
            245                 250                 255

Ala Arg Phe Lys Thr Phe Phe Asn Trp Pro Ser Ser Val Leu Val Asn
            260                 265                 270

Pro Glu Gln Leu Ala Ser Ala Gly Phe Tyr Tyr Val Gly Asn Ser Asp
        275                 280                 285

Asp Val Lys Cys Phe Cys Cys Asp Gly Gly Leu Arg Cys Trp Glu Ser
    290                 295                 300

Gly Asp Asp Pro Trp Val Gln His Ala Lys Trp Phe Pro Arg Cys Glu
305                 310                 315                 320
```

```
Tyr Leu Ile Arg Ile Lys Gly Gln Glu Phe Ile Arg Gln Val Gln Ala
            325                 330                 335

Ser Tyr Pro His Leu Leu Glu Gln Leu Leu Ser Thr Ser Asp Ser Pro
            340                 345                 350

Gly Asp Glu Asn Ala Glu Ser Ser Ile Ile His Phe Glu Pro Gly Glu
            355                 360                 365

Asp His Ser Glu Asp Ala Ile Met Met Asn Thr Pro Val Ile Asn Ala
            370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
            405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Arg
            435                 440

<210> SEQ ID NO 59
<211> LENGTH: 2286
<212> TYPE: DNA
<213> ORGANISM: Homo sapiens
<220> FEATURE:
<221> NAME/KEY: CDS
<222> LOCATION: (1)..(2094)
<223> OTHER INFORMATION: MLT region of SEQ ID NO:7

<400> SEQUENCE: 59 ata aag att act gta aac cca gag tca aag gca gtc ttg gct gga cag      48
Ile Lys Ile Thr Val Asn Pro Glu Ser Lys Ala Val Leu Ala Gly Gln
1               5                   10                  15 ttt gtg aaa ctg tgt tgc cgg gca act gga cat cct ttt gtt caa tat      96
Phe Val Lys Leu Cys Cys Arg Ala Thr Gly His Pro Phe Val Gln Tyr
            20                  25                  30 cag tgg ttc aaa atg aat aaa gag att cca aat gga aat aca tca gag     144
Gln Trp Phe Lys Met Asn Lys Glu Ile Pro Asn Gly Asn Thr Ser Glu
        35                  40                  45 ctt att ttt aat gca gtg cat gta aaa gat gca ggc ttt tat gtc tgt     192
Leu Ile Phe Asn Ala Val His Val Lys Asp Ala Gly Phe Tyr Val Cys
    50                  55                  60 cga gtt aat aac aat ttc acc ttt gaa ttc agc cag tgg tca cag ctg     240
Arg Val Asn Asn Asn Phe Thr Phe Glu Phe Ser Gln Trp Ser Gln Leu
65                  70                  75                  80 gat gtt tgc gac atc cca gag agc ttc cag aga agt gtt gat ggc gtc     288
Asp Val Cys Asp Ile Pro Glu Ser Phe Gln Arg Ser Val Asp Gly Val
                85                  90                  95 tct gaa tcc aag ttg caa atc tgt gtt gaa cca act tcc caa aag ctg     336
Ser Glu Ser Lys Leu Gln Ile Cys Val Glu Pro Thr Ser Gln Lys Leu
            100                 105                 110 atg cca ggc agc aca ttg gtt tta cag tgt gtt gct gtt gga agc cct     384
Met Pro Gly Ser Thr Leu Val Leu Gln Cys Val Ala Val Gly Ser Pro
        115                 120                 125 att cct cac tac cag tgg ttc aaa aat gaa tta cca tta aca cat gag     432
Ile Pro His Tyr Gln Trp Phe Lys Asn Glu Leu Pro Leu Thr His Glu
    130                 135                 140 acc aaa aag cta tac atg gtg cct tat gtg gat ttg gaa cac caa gga     480
Thr Lys Lys Leu Tyr Met Val Pro Tyr Val Asp Leu Glu His Gln Gly
145                 150                 155                 160 acc tac tgg tgt cat gta tat aat gat cga gac agt caa gat agc aag     528
Thr Tyr Trp Cys His Val Tyr Asn Asp Arg Asp Ser Gln Asp Ser Lys
                165                 170                 175
```

-continued

```
aag gta gaa atc atc ata gga aga aca gat gag gca gtg gag tgc act      576
Lys Val Glu Ile Ile Ile Gly Arg Thr Asp Glu Ala Val Glu Cys Thr
            180                 185                 190 gaa gat gaa tta aat aat ctt ggt cat cct gat aat aaa gag caa aca      624
Glu Asp Glu Leu Asn Asn Leu Gly His Pro Asp Asn Lys Glu Gln Thr
        195                 200                 205 act gac cag cct ttg gcg aag gac aag gtt gcc ctt ttg ata gga aat      672
Thr Asp Gln Pro Leu Ala Lys Asp Lys Val Ala Leu Leu Ile Gly Asn
    210                 215                 220 atg aat tac cgg gag cac ccc aag ctc aaa gct cct ttg gtg gat gtg      720
Met Asn Tyr Arg Glu His Pro Lys Leu Lys Ala Pro Leu Val Asp Val
225                 230                 235                 240 tac gaa ttg act aac tta ctg aga cag ctg gac ttc aaa gtg gtt tca      768
Tyr Glu Leu Thr Asn Leu Leu Arg Gln Leu Asp Phe Lys Val Val Ser
                245                 250                 255 ctg ttg gat ctt act gaa tat gag atg cgt aat gct gtg gat gag ttt      816
Leu Leu Asp Leu Thr Glu Tyr Glu Met Arg Asn Ala Val Asp Glu Phe
            260                 265                 270 tta ctc ctt tta gac aag gga gta tat ggg tta tta tat tat gca gga      864
Leu Leu Leu Leu Asp Lys Gly Val Tyr Gly Leu Leu Tyr Tyr Ala Gly
        275                 280                 285 cat ggt tat gaa aat ttt ggg aac agc ttc atg gtc ccc gtt gat gct      912
His Gly Tyr Glu Asn Phe Gly Asn Ser Phe Met Val Pro Val Asp Ala
    290                 295                 300 cca aat cca tat agg tct gaa aat tgt ctg tgt gta caa aat ata ctg      960
Pro Asn Pro Tyr Arg Ser Glu Asn Cys Leu Cys Val Gln Asn Ile Leu
305                 310                 315                 320 aaa ttg atg caa gaa aaa gaa act gga ctt aat gtg ttc tta ttg gat     1008
Lys Leu Met Gln Glu Lys Glu Thr Gly Leu Asn Val Phe Leu Leu Asp
                325                 330                 335 atg tgt agg aaa aga aat gac tac gat gat acc att cca atc ttg gat     1056
Met Cys Arg Lys Arg Asn Asp Tyr Asp Asp Thr Ile Pro Ile Leu Asp
            340                 345                 350 gca cta aaa gtc acc gcc aat att gtg ttt gga tat gcc acg tgt caa     1104
Ala Leu Lys Val Thr Ala Asn Ile Val Phe Gly Tyr Ala Thr Cys Gln
        355                 360                 365 gga gca gaa gct ttt gaa atc cag cat tct gga ttg gca aat gga atc     1152
Gly Ala Glu Ala Phe Glu Ile Gln His Ser Gly Leu Ala Asn Gly Ile
    370                 375                 380 ttt atg aaa ttt tta aaa gac aga tta tta gaa gat aag aaa atc act     1200
Phe Met Lys Phe Leu Lys Asp Arg Leu Leu Glu Asp Lys Lys Ile Thr
385                 390                 395                 400 gtg tta ctg gat gaa gtt gca gaa gat atg ggt aag tgt cac ctt acc     1248
Val Leu Leu Asp Glu Val Ala Glu Asp Met Gly Lys Cys His Leu Thr
                405                 410                 415 aaa ggc aaa cag gct cta gag att cga agt agt tta tct gag aag aga     1296
Lys Gly Lys Gln Ala Leu Glu Ile Arg Ser Ser Leu Ser Glu Lys Arg
            420                 425                 430 gca ctt act gat cca ata cag gga aca gaa tat tct gct gaa tct ctt     1344
Ala Leu Thr Asp Pro Ile Gln Gly Thr Glu Tyr Ser Ala Glu Ser Leu
        435                 440                 445 gtg cgg aat cta cag tgg gcc aag gct cat gaa ctt cca gaa agt atg     1392
Val Arg Asn Leu Gln Trp Ala Lys Ala His Glu Leu Pro Glu Ser Met
    450                 455                 460 tgt ctt aag ttt gac tgt ggt gtt cag att caa tta gga ttt gca gct     1440
Cys Leu Lys Phe Asp Cys Gly Val Gln Ile Gln Leu Gly Phe Ala Ala
465                 470                 475                 480 gag ttt tcc aat gtc atg atc atc tat aca agt ata gtt tac aaa cca     1488
Glu Phe Ser Asn Val Met Ile Ile Tyr Thr Ser Ile Val Tyr Lys Pro
```

```
ccg gag ata ata atg tgt gat gcc tac gtt act gat ttt cca ctt gat     1536
Pro Glu Ile Ile Met Cys Asp Ala Tyr Val Thr Asp Phe Pro Leu Asp
            500                 505                 510 cta gat att gat cca aaa gat gca aat aaa ggc aca cct gaa gaa act     1584
Leu Asp Ile Asp Pro Lys Asp Ala Asn Lys Gly Thr Pro Glu Glu Thr
        515                 520                 525 ggc agc tac ttg gta tca aag gat ctt ccc aag cat tgc ctc tat acc     1632
Gly Ser Tyr Leu Val Ser Lys Asp Leu Pro Lys His Cys Leu Tyr Thr
530                 535                 540 aga ctc agt tca ctg caa aaa tta aag gaa cat cta gtc ttc aca gta     1680
Arg Leu Ser Ser Leu Gln Lys Leu Lys Glu His Leu Val Phe Thr Val
545                 550                 555                 560 tgt tta tca tat cag tac tca gga ttg gaa gat act gta gag gac aag     1728
Cys Leu Ser Tyr Gln Tyr Ser Gly Leu Glu Asp Thr Val Glu Asp Lys
            565                 570                 575 cag gaa gtg aat gtt ggg aaa cct ctc att gct aaa tta gac atg cat     1776
Gln Glu Val Asn Val Gly Lys Pro Leu Ile Ala Lys Leu Asp Met His
        580                 585                 590 cga ggt ttg gga agg aag act tgc ttt caa act tgt ctt atg tct aat     1824
Arg Gly Leu Gly Arg Lys Thr Cys Phe Gln Thr Cys Leu Met Ser Asn
595                 600                 605 ggt cct tac cag agt tct gca gcc acc tca gga gga gca ggg cat tat     1872
Gly Pro Tyr Gln Ser Ser Ala Ala Thr Ser Gly Gly Ala Gly His Tyr
610                 615                 620 cac tca ttg caa gac cca ttc cat ggt gtt tac cat tca cat cct ggt     1920
His Ser Leu Gln Asp Pro Phe His Gly Val Tyr His Ser His Pro Gly
625                 630                 635                 640 aat cca agt aat gtt aca cca gca gat agc tgt cat tgc agc cgg act     1968
Asn Pro Ser Asn Val Thr Pro Ala Asp Ser Cys His Cys Ser Arg Thr
            645                 650                 655 cca gat gca ttt att tca agt ttc gct cac cat gct tca tgt cat ttt     2016
Pro Asp Ala Phe Ile Ser Ser Phe Ala His His Ala Ser Cys His Phe
        660                 665                 670 agt aga agt aat gtg cca gta gag aca act gat gaa ata cca ttt agt     2064
Ser Arg Ser Asn Val Pro Val Glu Thr Thr Asp Glu Ile Pro Phe Ser
675                 680                 685 ttc tct gac agg ctc aga att tct gaa aaa tgacctcctt gttttgaaa        2114
Phe Ser Asp Arg Leu Arg Ile Ser Glu Lys
        690                 695 gttagcataa ttttagatgc ctgtgaaata gtactgcact tacataaagt gagacattgt  2174
gaaaaggcaa atttgtatat gtagagaaag aatagtagta actgtttcat agcaaacttc  2234
aggactttga gatgttgaaa ttacattatt taattacaga cttcctcttt ct          2286
```

<210> SEQ ID NO 60
<211> LENGTH: 698
<212> TYPE: PRT
<213> ORGANISM: Homo sapiens

<400> SEQUENCE: 60

Ile Lys Ile Thr Val Asn Pro Glu Ser Lys Ala Val Leu Ala Gly Gln
1               5                   10                  15

Phe Val Lys Leu Cys Cys Arg Ala Thr Gly His Pro Phe Val Gln Tyr
            20                  25                  30

Gln Trp Phe Lys Met Asn Lys Glu Ile Pro Asn Gly Asn Thr Ser Glu
        35                  40                  45

Leu Ile Phe Asn Ala Val His Val Lys Asp Ala Gly Phe Tyr Val Cys
    50                  55                  60

-continued

```
Arg Val Asn Asn Asn Phe Thr Phe Glu Phe Ser Gln Trp Ser Gln Leu
 65                  70                  75                  80

Asp Val Cys Asp Ile Pro Glu Ser Phe Gln Arg Ser Val Asp Gly Val
                 85                  90                  95

Ser Glu Ser Lys Leu Gln Ile Cys Val Glu Pro Thr Ser Gln Lys Leu
            100                 105                 110

Met Pro Gly Ser Thr Leu Val Leu Gln Cys Val Ala Val Gly Ser Pro
        115                 120                 125

Ile Pro His Tyr Gln Trp Phe Lys Asn Glu Leu Pro Leu Thr His Glu
    130                 135                 140

Thr Lys Lys Leu Tyr Met Val Pro Tyr Val Asp Leu Glu His Gln Gly
145                 150                 155                 160

Thr Tyr Trp Cys His Val Tyr Asn Asp Arg Asp Ser Gln Asp Ser Lys
                165                 170                 175

Lys Val Glu Ile Ile Ile Gly Arg Thr Asp Glu Ala Val Glu Cys Thr
            180                 185                 190

Glu Asp Glu Leu Asn Asn Leu Gly His Pro Asp Asn Lys Glu Gln Thr
        195                 200                 205

Thr Asp Gln Pro Leu Ala Lys Asp Lys Val Ala Leu Leu Ile Gly Asn
    210                 215                 220

Met Asn Tyr Arg Glu His Pro Lys Leu Lys Ala Pro Leu Val Asp Val
225                 230                 235                 240

Tyr Glu Leu Thr Asn Leu Leu Arg Gln Leu Asp Phe Lys Val Val Ser
                245                 250                 255

Leu Leu Asp Leu Thr Glu Tyr Glu Met Arg Asn Ala Val Asp Glu Phe
            260                 265                 270

Leu Leu Leu Leu Asp Lys Gly Val Tyr Gly Leu Leu Tyr Tyr Ala Gly
        275                 280                 285

His Gly Tyr Glu Asn Phe Gly Asn Ser Phe Met Val Pro Val Asp Ala
    290                 295                 300

Pro Asn Pro Tyr Arg Ser Glu Asn Cys Leu Cys Val Gln Asn Ile Leu
305                 310                 315                 320

Lys Leu Met Gln Glu Lys Glu Thr Gly Leu Asn Val Phe Leu Leu Asp
                325                 330                 335

Met Cys Arg Lys Arg Asn Asp Tyr Asp Asp Thr Ile Pro Ile Leu Asp
            340                 345                 350

Ala Leu Lys Val Thr Ala Asn Ile Val Phe Gly Tyr Ala Thr Cys Gln
        355                 360                 365

Gly Ala Glu Ala Phe Glu Ile Gln His Ser Gly Leu Ala Asn Gly Ile
    370                 375                 380

Phe Met Lys Phe Leu Lys Asp Arg Leu Leu Glu Asp Lys Lys Ile Thr
385                 390                 395                 400

Val Leu Leu Asp Glu Val Ala Glu Asp Met Gly Lys Cys His Leu Thr
                405                 410                 415

Lys Gly Lys Gln Ala Leu Glu Ile Arg Ser Ser Leu Ser Glu Lys Arg
            420                 425                 430

Ala Leu Thr Asp Pro Ile Gln Gly Thr Glu Tyr Ser Ala Glu Ser Leu
        435                 440                 445

Val Arg Asn Leu Gln Trp Ala Lys Ala His Glu Leu Pro Glu Ser Met
    450                 455                 460

Cys Leu Lys Phe Asp Cys Gly Val Gln Ile Gln Leu Gly Phe Ala Ala
465                 470                 475                 480
```

-continued

```
Glu Phe Ser Asn Val Met Ile Ile Tyr Thr Ser Ile Val Tyr Lys Pro
                485             490             495

Pro Glu Ile Ile Met Cys Asp Ala Tyr Val Thr Asp Phe Pro Leu Asp
            500             505             510

Leu Asp Ile Asp Pro Lys Asp Ala Asn Lys Gly Thr Pro Glu Glu Thr
            515             520             525

Gly Ser Tyr Leu Val Ser Lys Asp Leu Pro Lys His Cys Leu Tyr Thr
            530             535             540

Arg Leu Ser Ser Leu Gln Lys Leu Lys Glu His Leu Val Phe Thr Val
545             550             555             560

Cys Leu Ser Tyr Gln Tyr Ser Gly Leu Glu Asp Thr Val Glu Asp Lys
                565             570             575

Gln Glu Val Asn Val Gly Lys Pro Leu Ile Ala Lys Leu Asp Met His
            580             585             590

Arg Gly Leu Gly Arg Lys Thr Cys Phe Gln Thr Cys Leu Met Ser Asn
            595             600             605

Gly Pro Tyr Gln Ser Ser Ala Ala Thr Ser Gly Gly Ala Gly His Tyr
            610             615             620

His Ser Leu Gln Asp Pro Phe His Gly Val Tyr His Ser His Pro Gly
625             630             635             640

Asn Pro Ser Asn Val Thr Pro Ala Asp Ser Cys His Cys Ser Arg Thr
                645             650             655

Pro Asp Ala Phe Ile Ser Ser Phe Ala His His Ala Ser Cys His Phe
            660             665             670

Ser Arg Ser Asn Val Pro Val Glu Thr Thr Asp Glu Ile Pro Phe Ser
            675             680             685

Phe Ser Asp Arg Leu Arg Ile Ser Glu Lys
            690             695
```

MOLECULAR CHARACTERIZATION OF CHROMOSOME TRANSLOCATION T(11;18)(Q21;Q21) AND ITS CORRELATION TO CARCINOGENESIS

This application is a continuation of U.S. patent application Ser. No. 09/579,692, filed Mar. 26, 2000, now U.S. Pat. No. 6,689,875, which claims priority from Provisional Patent Application No. 60/138,834, filed Jun. 9, 1999.

BACKGROUND OF THE INVENTION

Technical Field

The invention relates to the fields of medicine and diagnostics. More in particular, the invention relates to medicine and the diagnosis of tumors.

Recurrent translocations acquired in a process of transformation are well recognized in nodal B-cell lymphomas. These translocations characterize distinct subtypes of disease and involve genes controlling cell proliferation and apoptosis. BCL2, which suppresses apoptosis, was cloned from the t(14;18)(q21;q32) found in most cases of follicular B-cell lymphoma, whereas translocations involving the BCL1/CyclinD1 gene on chromosome 11q13 are seen in nearly all cases of mantle cell lymphoma.[1]

By contrast, the genetic mechanisms underlying the genesis and disease progression of extranodal marginal zone B-cell lymphomas of the mucosa-associated lymphoid tissue (MALT) type, a recently recognized distinct subtype of B-cell Non-Hodgkin's Lymphoma's (NHL), are not known.[2] MALT lymphomas account for five to ten percent of all NHLs and the vast majority of lymphomas arising at extranodal sites. They originate in a setting of chronic inflammation triggered by chronic infection or autoimmune disorders, such as *Helicobacter pylori* gastritis, Sjögren's syndrome, and Hashimoto's thyroiditis.[3] In vitro experiments have shown that *H. pylori* specific T-cells provide contact-dependent help for the growth of the malignant B-cells of gastric MALT.[4] The etiological link between low-grade gastric MALT lymphomas and *H. pylori* infection has also been demonstrated by the regression of some cases with antibiotic therapy.[5,6] The preferential use of immunoglobulin variable region genes ($V_H$) associated with autoimmune disorders indicates that some MALT lymphomas may arise from autoreactive B-cells.[7,8]

Since biopsies of these lymphomas are relatively rarely subjected to cytogenetic analysis and their in vitro proliferation is often poor, abnormal karyotypic data have been published for only 46 low-grade MALT lymphomas,[9-17] 5 extranodal small lymphocytic lymphomas of probable marginal zone origin,[18-20] and 23 high-grade gastric MALT lymphomas.[14,15] Recurrent abnormalities in these cases include trisomies of chromosomes 3, 7, 12, and 18,[11,17,21] the t(1;14)(p22;q32) which has been described in two cases[17] and the t(11;18)(q21;q21). The t(11;18)(q21;q21) has been detected in 15 out of the 51 low-grade lymphomas arising from various extranodal sites[9,12,14,18-20] but in none of the high-grade MALT lymphomas or any other subtype of NHL. In the largest cytogenetic series, this translocation has been found in 7 out of 13 cases of low-grade MALT lymphomas with an abnormal karyotype.[14] These data clearly indicate that the t(11;18) represents the most frequent structural abnormality in low-grade MALT lymphomas and seems to specifically characterize this disease entity. An attempt to delineate the breakpoint at 18q21.1 has been described by Akagi et al. (Genes, Chromosomes and Cancer, 24 (1999): 315-321). A detailed characterization, however, is urgently needed.

BRIEF SUMMARY OF THE INVENTION

In one aspect, the present invention provides a detailed molecular genetic characterization of the 11q21 and 18q21 breakpoint regions in MALT lymphomas characterized by the t(11;18)(q21;q21). The invention further identifies that the API2 gene, also known as c-IAP2,[22] HIAPI[23] and MIHC,[24] an inhibitor of apoptosis, and a novel gene on 18q21, named MLT, are rearranged in this translocation. The invention also identifies that truncation of the API2 gene distal to its three BIR domains and fusion of this truncated gene with the carboxy-terminal region of MLT may lead to increased inhibition of apoptosis and thereby confer a survival benefit to MALT type B-cell lymphomas. In other words, the present invention discloses that, surprisingly, truncation of the API2 gene and fusion to the new MLT gene is crucial for the development of MALT type B-cell lymphomas.

In one aspect, the invention teaches that the t(11;18)(q21;q21) associated with extranodal marginal zone B-cell lymphomas of the MALT type results in the expression of a chimeric transcript fusing 5'-API2 on chromosome 11 to 3'-MLT on chromosome 18. The occurrence of the t(11;18) translocation in not less than 17 out of 51 published cases of low-grade MALT lymphomas[9,12,14,18-20] including the two cases described herein, along with its presence as the sole cytogenetic abnormality in 16 out of the 17 reported cases, indicates that the t(11;18) represents one of the main recurrent, disease-specific translocations in NHL.

Several observations point to the API2-MLT fusion as the oncogenic lesion underlying the t(11;18). The chimeric cDNA was cloned from two independent tumors. In one case, the genomic breakpoints were also cloned and the structure of both genes and the localization of the breakpoints are in agreement with the expression of the fusion transcript. The cryptic deletion of the 3' part of API2 in case 1 precludes the expression of a reciprocal MLT-API2 transcript in this case. As a result of the deletion, the 5'-end of the MLT gene is fused to the 5'-end of the MMP20 gene on the der(18). As both genes are present on opposite strands of the DNA, no MLT-MMP20 transcript is expressed. Furthermore, FISH experiments with PACs for respectively MLT, API2 and MMP20 clearly suggest that, in case 2, a balanced translocation occurred not involving a break in the MMP20 gene, further arguing against any significance of the MLT-MMP20 fusion.

API2 belongs to the family of inhibitors of apoptosis proteins ("IAP"), which play an evolutionary conserved role in regulating programmed cell death in diverse species (International Patent Application WO 97/06182 to Rothe and Goeddel). The IAP genes were first identified in baculoviruses in which they demonstrated an ability to suppress the host cell apoptotic response to viral infection.[33] Subsequently, five human IAP relatives have been described: NIAP, API1 (also known as cIAP1, HIAP2, MIHB), API2 (cIAP2, HIAP1, MIHC), XIAP-hILP and survivin.[22-24,34-37] The common structural features of all IAP family members is a motif termed baculovirus IAP repeat ("BIR") occurring in one to three copies, a caspase recruitment domain or CARD[30] located between the BIR domain(s) and a carboxy-terminal zinc binding RING finger domain[31] that is present in all IAPs with the exception of NIAP and survivin. The human API1 and API2 proteins were originally identified as proteins that are recruited to the cytosolic domain of the tumor necrosis factor (TNF) receptor II via their association with the TNF-associated factor (TRAF) proteins, TRAF-1 and TRAF-2,[22] and have been subsequently shown to suppress different apoptotic pathways by inhibiting distinct caspases, such as caspase-3, caspase-7, and pro-caspase-9.[35,38]

The function of the novel MLT gene (also known as "MALT1") located on chromosome 18q21 is not yet known. Its closest homologue is a hypothetical *C. elegans* gene. The carboxy-terminal part of this gene is characterized by the presence two Ig-like C2-type domains and a domain similar to the murine Ig gamma chain VDJ4 sequence (Accession no. M13070). The C2 domains are only present in the longer fusion cDNA of case 2 and thus probably have no functional significance in the tumor.

The molecular mechanism of action of the API2-MLT fusion remains to be elucidated. Without being limited by theory, it is hypothesized that the fusion protein resulting from the t(11;18) may lead to increased inhibition of apoptosis and thereby confer a survival advantage to MALT lymphomas and allow antigen-independent proliferation. Indeed, MALT lymphomas have been shown to display low levels of apoptosis[39] and to escape from FAS-mediated apoptosis[40] and about 20% of low-grade MALT lymphomas do not respond to *H. pylori* eradication therapy.[6] The truncation of API2 after the BIR domains could release their anti-apoptotic effects from regulation by the CARD and RING domains. Recent studies have shown that the BIR domain-containing regions of API1 and API2 are sufficient for inhibition of caspases and suppression of apoptosis.[35] The BIR domains of one of the Drosophila homologues ("DIAP1") were demonstrated to suppress apoptosis in the Drosophila eye disk, whereas the full-length protein exhibited less activity. Moreover, transgenic flies over-expressing the RING domain alone exhibited increased cell death in the eye, suggesting that the RING domain may act as a negative regulator of cell death suppression in some instances.[34] On the other hand, a specific role for the carboxy-terminal MLT domain is suggested by its consistent presence in the fusion and by the recurrency of the t(11;18) in MALT lymphoma. This is supported by the observation that full-length API1 and API2 were somewhat more potent in caspase inactivation than constructs lacking the RING domain.[35] It is possible that the presence of the MLT domain would stabilize the fusion protein, increase its affinity for protein interaction or influence its subcellular localization, thereby modulating its interactions with other proteins.

The mechanism of gene deregulation by the t(11;18) differs from that seen in most of the B-cell lymphoma-associated translocations, which involve one of the immunoglobulin loci on 14q32, 2p12, or 22q11 and lead to deregulated expression of the incoming oncogene due to the proximity of potent B-cell transcriptional enhancers within the immunoglobulin loci.[41] In this case, the expression of the fusion gene is driven from the promoter of its 5' partner, API2. This agrees with the observation that API2 mRNA is highly expressed in adult lymphoid tissues, including spleen, thymus, and peripheral blood lymphocytes, and also in fetal lung and kidney.[23] It is also interesting to note that the IAP family member survivin is strongly expressed in apoptosis-regulated human fetal tissues, but not in terminally differentiated adult tissues.[42] Survivin becomes prominently expressed in transformed cell lines and in most human cancers. Survivin expression was also found in 50% of high-grade NHL (centroblastic, immunoblastic) but not in low-grade lymphomas (lymphocytic).[37]

At the genomic level, the rearrangements appear to be heterogeneous. The breakpoint in MLT occurred in two different introns for both cases. In the API2 gene the breakpoint occurred in the same intron for both cases, but it was associated with the deletion of the 3'-end of the gene in only one tumor. The cytogenetic analysis of MALT lymphoma is often hampered by their poor proliferation in vitro. However, the physical maps and the genomic clones that the present invention teaches allow the development of a wide variety of sensitive detection methods for this rearrangement, such as but not limited to interphase FISH assays and assays based on the specific amplification of nucleic acid encompassing the t(11: 18) breakpoint. Alternatively, the fusion mRNA or the fusion protein provides new molecular targets for diagnosis.

In one aspect, the invention provides a method for determining whether a tissue sample or an analogue and/or derivative thereof comprises a cell with a chromosome (11:18) translocation associated with malignancies such as MALT lymphomas, the method comprising subjecting nucleic acid from the sample to an amplification reaction using a primer that is complementary to a nucleic acid sequence which in humans lies on chromosome 11 region q21-22.3 and a primer that is complementary to a nucleic acid sequence which in humans lies on chromosome 18 region q21.1-22, and determining the presence of any amplified product. Preferably, the tissue sample is taken from a human individual. Preferably, the individual is suffering from or at risk of suffering from a disease.

The nucleic acid may comprise chromosomal DNA, RNA or any other type of nucleic acid. With the knowledge of the region in which the (11:18) translocation occurs, a person skilled in the art is capable of developing specific nucleic acid amplification methods that allow the unambiguous detection of the translocation in a tissue sample. Such assays may be developed based on nucleic acid sequence information presented here. However, it is clear that using the teachings of the present invention, i.e., the identification of the breakpoint and the methods and means to do so, additional nucleic acid sequence information on the region surrounding the breakpoint can be obtained and the use of such sequence information for the development of detection assays for the translocation falls within the scope of the present invention. The term "complementary primer" means a primer that can hybridize to another sequence under relatively mild hybridization conditions, i.e., hybridization conditions that allow nucleic acids with sequences with some mismatches to hybridize to each other. The number of mismatches among others determines the specificity and the efficiency of polymerization. A complementary primer should comprise not more than 30% mismatches, preferably not more than 20% and more preferably not more than 10%. Preferably, the primer does not comprise mismatches.

Amplification methods that may be used in a method of the invention include but are not limited to polymerase chain reaction, NASBA and intracellular PCR.

Figure 1:
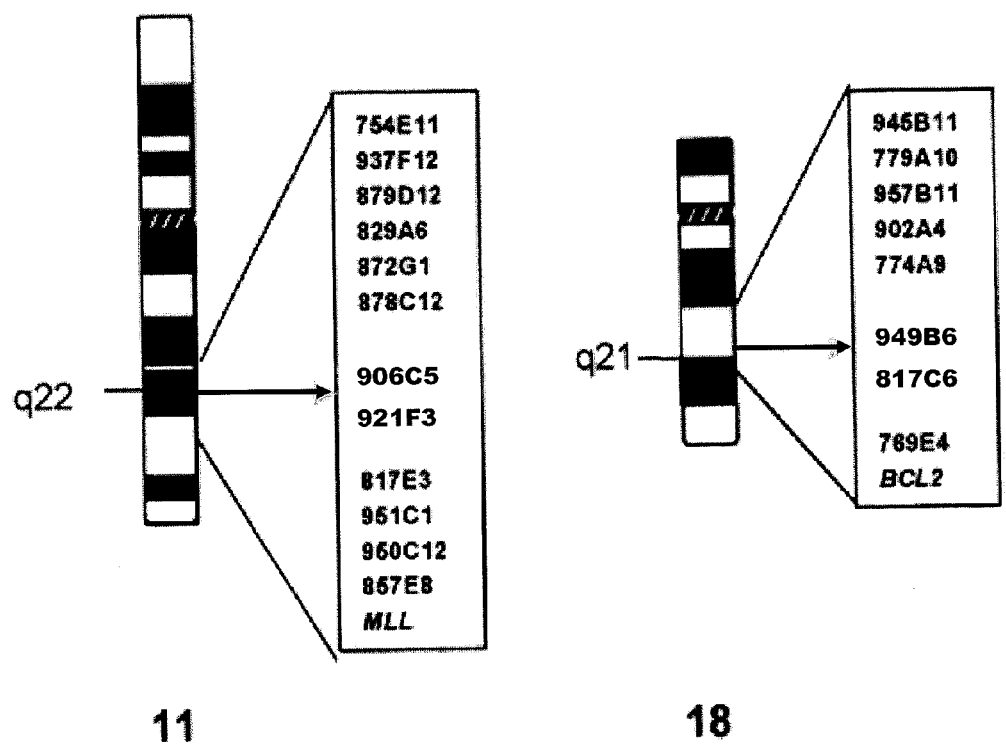
FIG. 1: Cytogenetics and YAC characterization of the t(11; 18).

Panel B illustrates the structure of the different fusion cDNAs. On top, the structure of API2 is shown with 3 amino-terminal BIR domains separated from the carboxy-terminal RING domain by a CARD domain. The API2 cDNA is truncated after the third BIR domain and fused in frame to MLT the nucleotides shown below the structure correspond to nucleotides 1434 to 1446 and 2029 to 2045 of SEQ ID NO:7, the amino acids corresponds to 438 to 441 (the serine) and 637 to 641 of SEQ ID NO:8, (the case 1 junction produces a codon for Asparagine (N)). As a result of the heterogeneity of the genomic breakpoints in case 2, 582 additional nucleotides, encoding two Ig-like C2 domains of MLT, are present in this fusion. An Ig gamma VDJ4-like sequence in MLT is shown by a cross-hatched box. The sequence and translation of the different junction fragments is shown underneath each cDNA; in case 1 the nucleotides correspond to nucleotides 1434 to 1446 fused to nucleotides 2029 to 2045 of SEQ ID NO:7 and the amino acids correspond to 438 to 441 (the serine) and 637 to 641 of SEQ ID NO:8 (the junction produces a codon for Asparagine (N)); in case 2 the nucleotides correspond to nucleotides 1434 through 1463 of SEQ ID NO:7 and amino acids 438 through 447 of SEQ ID NO:8.

FIG. 3A-D: FISH Mapping of the chromosome 11 and 18 breakpoints. A: the hybridization signals of YAC 921 F3 and the BamHI fragment H of PAC 152M5 are both split by the translocation in case 1. Signals of both probes are visible on the derivative chromosomes 11 and 18. B: in case 2, fragment D of PAC 152M5 shows split signals. The centromeric probes for chromosomes 11 and 18 appear. C: in case 1, PAC 532024 is seen on the normal chromosome 11 and on the derivative chromosome 11 (C), whereas this probe is split by the translocation in case 2 (D). The signals of the centromeric probes are shown.

Figure 4A:
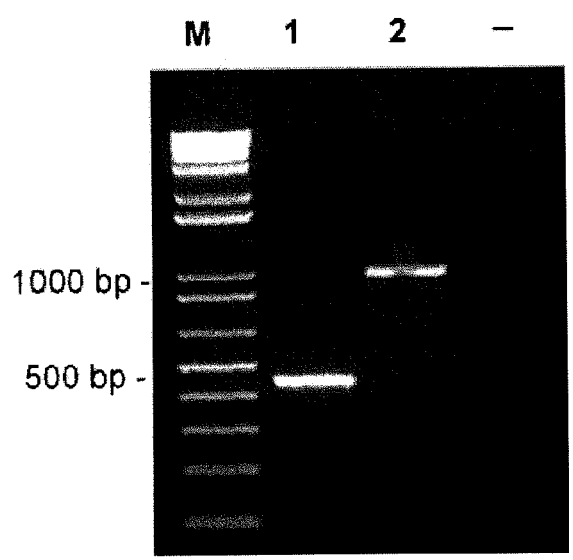
Figure 4B:
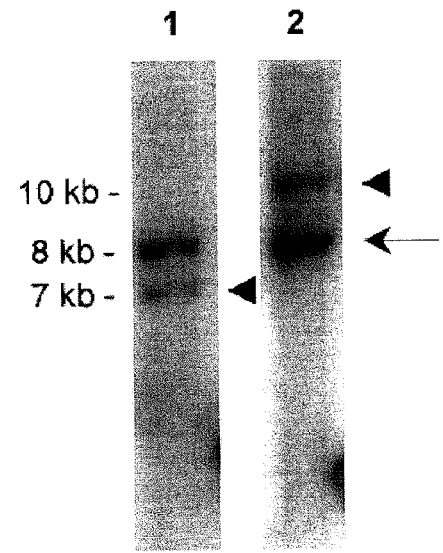

FIG. 4A-B: Molecular characterization of the fusions. (A) shows the API2-MLT products obtained by RT-PCR from case 1 and case 2. (B) shows the Southern blot detecting the rearranged EcoRI fragments of case 1. The probes were derived from an 8 kb EcoRI clone from chromosome 18 spanning the breakpoint (see FIG. 2A center). Lane 1 shows hybridization with the probe derived proximally to the breakpoint; lane 2 shows hybridization with the probe derived distally to the breakpoint. The arrow shows the normal 8 kb EcoRI fragment; the arrowheads show the chimeric fragments.

FIG. 5A-E: Sequence of the API2-MLT chimeric cDNA SEQ ID NO:7.

Figure 6A:
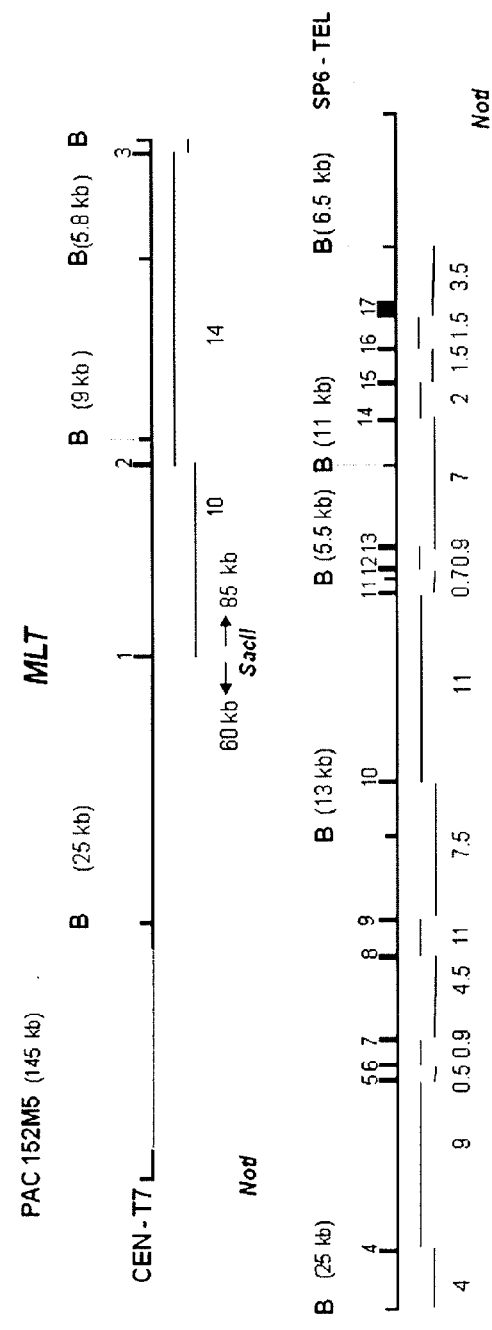
Figure 6B:
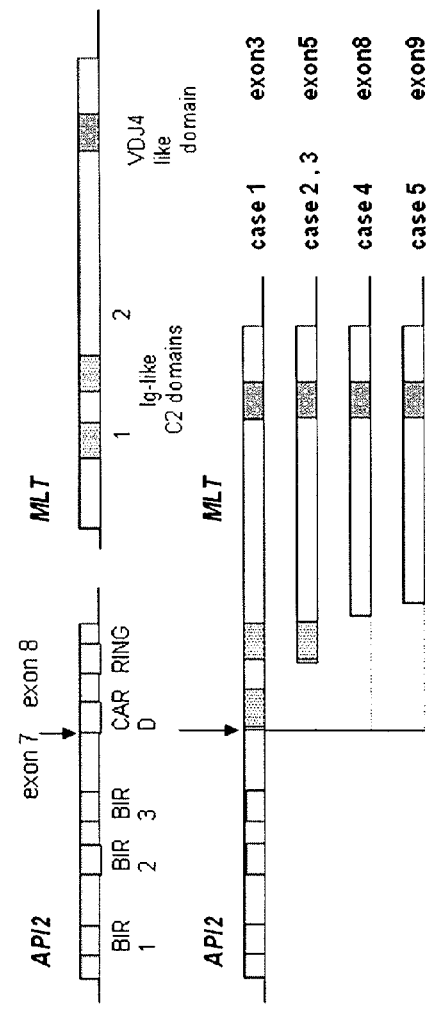

FIG. 6A-B: A) Genomic structure of the MLT gene. A (partial) BamHI and (B) restriction map of PAC 1 52M5 is depicted. The sizes of ordered BamHI fragments are indicated; the last BamHI site of the first lane corresponds to the first one on the second lane. Solid rectangles represent the different MLT exons; their respective number is marked above. Solid lines delineate the MLT introns; their estimated size is specified underneath. The unique SacII site is present in exon 1 of MLT; the size of the fragments obtained after NotI/SacII digestion are indicated. B) Features of API2, MLT and observed API2-MLT fusions of the five cases characterized are shown. API2 contains three amino-terminal BIR domains separated from the carboxy-terminal RING domain by a CARD domain. The arrow indicates the position of the API2 breakpoint observed in all cases, between exon 7 and exon 8. MLT harbors two Ig-like C2 domains and an Ig gamma VDJ4-like sequence.

FIG. 7A-B: A) The chromosome 11 breakpoints on the der(11) and sequence features of intron 7 of API2. Numbering is according to Acc. No. AF178945. B) Schematic representation of the genomic structure of the API2-MLT and MLT-API2 fusion fragments in five cases (not drawn to scale). Grey and black boxes represent API2 and MLT exons respectively; white boxes represent repetitive elements. Solid black bars define deletions associated with the t(11;18) translocation. When known, the distance between the breakpoint and MLT exons is indicated. Abbreviations for repetitive elements (matching repeat # repeat class/family): AluSx # SINE/Alu (Sx), AluJo # SINE/Alu (Jo), AluSg/x # SINE/Alu (Sg/x), AluY # SINE/Alu (Y), L2 # LINE/L2, MIR # SINE/MIR, FLAM_A # SINE/Alu, L1MC3 # LINE/L1.

DETAILED DESCRIPTION OF THE INVENTION

In a preferred embodiment, the amplified product comprises a linked nucleic acid comprising at least part of nucleic acid encoding a MALT-Lymphoma associated Translocation (MLT) protein and at least part of nucleic acid encoding apoptosis inhibitor 2 (API2).

In a preferred embodiment, the tissue sample comprises a lymphocyte, preferably an activated lymphocyte. In a preferred embodiment, the tissue sample comprises digestive tract cells and/or stomach cells.

In another aspect, the invention provides an isolated and/or recombinant nucleic acid encoding a proteinaceous molecule comprising at least API2 or a functional part, derivative and/or analogue thereof fused to at least one other proteinaceous molecule. The other proteinaceous molecule may be any proteinaceous molecule. Preferably, the other proteinaceous molecule comprises a MALT-Lymphoma associated Translocation (MLT) protein or a functional part, derivative and/or analogue thereof. Preferably, the nucleic acid molecule comprises in humans a sequence as depicted in FIG. 5 or a functional part, derivative and/or analogue thereof.

A nucleic acid of the invention may further comprise other nucleic acid. Other nucleic acid may facilitate cloning or amplification in bacteria. Preferably, the other nucleic acid comprises nucleic acid corresponding in humans to chromosome 11 region q21-22.3 or a functional part, derivative and/ or analogue thereof. In this way, the nucleic acid has advantageous properties for FISH analysis. Preferably, the other nucleic acid comprises nucleic acid corresponding in humans to chromosome 18 region q21.1-22 or a functional part, derivative and/or analogue thereof. In this way, the nucleic acid has advantageous properties for FISH analysis.

The invention further provides a proteinaceous molecule encoded by a nucleic acid of the invention, or a functional part, derivative and/or analogue thereof. The protein may be advantageously used for the at least in part transforming a primary cell, preferably a B-cell and thus enabling and/or facilitating the generation of in vitro growing cell derivatives of the cell. One method of providing a cell with a proteinaceous molecule is through providing the cell with an expressible nucleic acid encoding the proteinaceous molecule and culturing the cell to obtain expression of the proteinaceous molecule. Preferably, the proteinaceous molecule comprises a sequence that, in humans, is a sequence as depicted in FIG. 5, or a functional part, derivative and/or analogue thereof.

In another aspect, the invention provides an isolated recombinant nucleic acid encoding an MLT protein that, in humans, comprises a sequence as depicted in FIG. 5 or a functional part, derivative and/or analogue thereof. The invention further provides an MLT protein encoded by a nucleic acid mentioned heretofore or a functional part, derivative and/or analogue thereof.

The invention further provides an antibody specific for a proteinaceous molecule according to the invention. It is clear to the person skilled in the art that antibodies can be generated in many ways once a suitable antigen has been identified. Antibodies can be generated through, for instance, the immunization of an animal or human with a proteinaceous molecule of the invention. Alternatively, suitable peptides can be generated and used using standard protocols used in the art to generate antibodies in a mammal. However, antibodies can also be generated completely artificially from, for instance, libraries of synthetic antibodies, single-chain antibodies, FAB fragment libraries, etc. Suitable antibodies may be isolated from such libraries through techniques known in the art. Furthermore, for the purpose of this invention, any proteinaceous molecule capable of binding to a proteinaceous molecule of the invention is considered an antibody.

In another aspect, the invention provides the use of a nucleic acid of the invention and/or an antibody of the invention as a probe. The term "probe" refers to a means for detection. A nucleic acid of the invention may be used as a probe, for instance but not limited to, for hybridization to Southern Blot DNA of cells or for in situ hybridization of cells to determine the presence of DNA complementary to the nucleic acid. Information regarding the presence of such DNA may be used for determining the presence or absence of cells comprising the (11:18) translocation. Similarly, an antibody of the invention may be used for the determination of cells expressing a proteinaceous molecule of the invention.

In another aspect, the invention provides a method for at least in part improving an immune response against an antigen comprising providing an immune cell comprising an immune property specific for the antigen with an expressible nucleic acid of the invention.

In yet another aspect, the invention provides a method for at least in part preventing apoptosis in a cell comprising providing the cell with an expressible nucleic acid of the invention.

In yet another aspect, the invention provides a nucleic delivery vehicle comprising a nucleic acid according to the invention. Preferably, the nucleic acid delivery vehicle comprises a virus particle, preferably an adenovirus particle, an adeno-associated virus particle and/or a retrovirus particle.

In yet another aspect, the invention provides a cell comprising a nucleic acid according to the invention and/or a proteinaceous molecule according to the invention.

In yet another aspect, the invention provides a transgenic animal comprising a nucleic acid according to the invention. The transgenic animal can be any known non-human animal and is preferably a mouse as is exemplified further.

The invention is further explained by the use of the following, illustrative Examples.

EXAMPLES

1. Characterization of the 11q21 and 18q21 Translocation and Cloning of the Fusion Genes Material and Methods Tumor Specimens Two cases of low-grade extranodal gastrointestinal MALT lymphomas displaying the t(11;18)(q21;q21) were selected from the files of the Center for Human Genetics, University of Leuven, Belgium, and the Department of Hematology, University of Salamanca, Spain, based on the availability of metaphase spreads and frozen tumor tissue. Case 1 presented with an extended multifocal gastrointestinal MALT lymphoma involving the stomach, the small and large bowel, and the mesenteric lymph nodes. Case 2 was diagnosed with a gastric MALT lymphoma with secondary involvement of the spleen, the bone marrow, and the peripheral blood. Both cases revealed *H. pylori*-associated gastritis and showed the typical morphology and immunophenotype of marginal zone B-cell lymphomas of MALT type including the characteristic tumor cell composition, extension of the marginal zones by tumor cells, follicular colonization, lymphoepithelial lesions, expression of IgM, CD 19, CD2O, Igk light chain restriction, and negativity for CD5, CD 10, and CD23.[2]

Cytogenetic Analysis

Cytogenetic analysis was performed as described[11] utilizing tissue of a small bowel biopsy (case 1) and the spleen specimen (case 2). Both cases showed the t(11;18)(q21;q21) as the sole cytogenetic abnormality (case 1: 46,XY,t(11;18)(q21;q21) [17]/46,XY [3]; case 2: 46,XX,t(11;18)(q21;q21) [6]/46,X [14]). Fluorescence in situ hybridization (FISH) was performed as previously described.[25] Chromosomes 11 and 18 were identified by cohybridization with chromosome 11 (pLC11A) and 18 (L1.84) specific alpha-satellite probes in combination with G-banding using 4,6-diamidino-2-phenylindole-dihydrochloride (DAPI) counterstain.

Yeast Artificial Chromosome (YAC) Clones

YAC clones derived from the Centre dEtude du Polymorphism Human (CEPH) human mega YAC library were selected from the YAC contig reported by Chumakov et al.[26] and data obtained from the Whitehead Institute/MIT Center for Genome Research. In addition, YAC A1 53A6 hybridizing to the BCL2 gene located at 18q21[27] and a probe specific for the MLL gene on 11q23 (Oncor, Gaithersburg, Md.) were used. Human YAC inserts were selectively amplified using Alu-polymerase chain reaction (PCR).[28] In order to confirm their cytogenetic position and to determine the relative order of the YAC clones, pairs of differentially labeled YACs were hybridized to normal metaphase spreads obtained from PHA-stimulated peripheral blood lymphocytes of a healthy donor.

P1 Artificial Chromosome (PAC) and Plasmid Clones

PAC clones were isolated by screening high-density filters from the RPCI libraries with $^{32}$P-labeled probes. A walking strategy was used to extend the map. PAC end-fragments were rescued using a vectorette ligation approach.[29] The presence of the STS in the relevant PACs was confirmed by PCR and each PAC was analyzed by FISH on normal metaphase spreads.

BamHI subclones of PAC 152M5 were generated by ligation of gel-purified fragments in pUC18 (Pharmacia Biotech, Uppsala, Sweden) and transformation into XL10-gold cells (Stratagene, La Jolla, Calif.). A BamHI restriction map was generated by comparing the sequence of the ends of the BamHI fragments to the sequence of random 1 kb subclones selected for containing the BamHI restriction sites. To generate random subclones of PAC 152M5, DNA was sheared by sonication and the fraction around 1 kb was gel-purified (Qiaquick Gel Extraction, Qiagen), blunted and ligated in pUC18, and transformed into XL1-blue cells.

Reverse Transcriptase (RT)-PCR and Cloning

Total RNA was extracted from respectively tumor-infiltrated gastrointestinal and splenic tissue using the Trizol Reagent (Life Technologies, Inc., Rockville, Md.). First strand cDNA was reverse transcribed from 1 μg of total RNA with Murine Moloney Leukemia Virus reverse transcriptase (Life Technologies, Inc., Rockville, Md.) according to standard procedures using a random hexamer primer. After size fractionation on Microspin S-400 HR columns (Pharmacia Biotech), a poly-A tail was added to the first strand cDNA with dATP and terminal deoxynucleotidyl transferase (Boehringer Mannheim, Mannheim, Germany). Double-stranded cDNA was then generated using standard procedures with primer R2T8 (5' CCAGTGAGCAGAGTGACGAGGACTC-GAGCTCAAGCTTTTTTTT 3' (SEQ ID NO:1)). Nested PCR was performed respectively using primers MLTr1 (5' CCTTCTGCAACTTCATCCAG 3' (SEQ ID NO:2)) and MLTr2 (5' ATGGATTTGGAGCATCAACG 3' (SEQ ID NO:3)) in combination with primers R2F1 (5' CCAGTGAG-CAGAGTGACG 3' (SEQ ID NO:4)) and R2F2 (5' GAG-GACTCGAGCTCAAGC 3' (SEQ ID NO:5)). Amplification products were cloned in pGEM T-easy (Promega, Madison, Wis.).

The API2-MLT fusion was confirmed by RT-PCR on patient RNA using the Titan RT-PCR system (Boehringer Mannheim) with primers API2fl (5' CCAAGTGGTTTC-CAAGGTGT 3' (SEQ ID NO:6)) and MLTr2 and by sequence analysis of the cloned amplification products. A partial MLT cDNA was isolated by 3' RACE on cDNA of patient 1. Several overlapping clones were analyzed to obtain the 3' end sequences of MLT (Genbank accession no. AF 130356).

Results

FISH Characterization of the 11q21 and 18q21 Translocation

Twelve YACs derived from the chromosomal region 11q12-22.3 and the MLL probe were hybridized to metaphase spreads of case 1. FIG. 1 shows their relative position in relation to the t(11;18) breakpoints. The hybridization signals of YACs 906C5 and 921F3 were split by the translocation. Subsequent analysis showed that YACs 906C5 and 921F3 also spanned the translocation breakpoint of case 2.

Figure 2A:
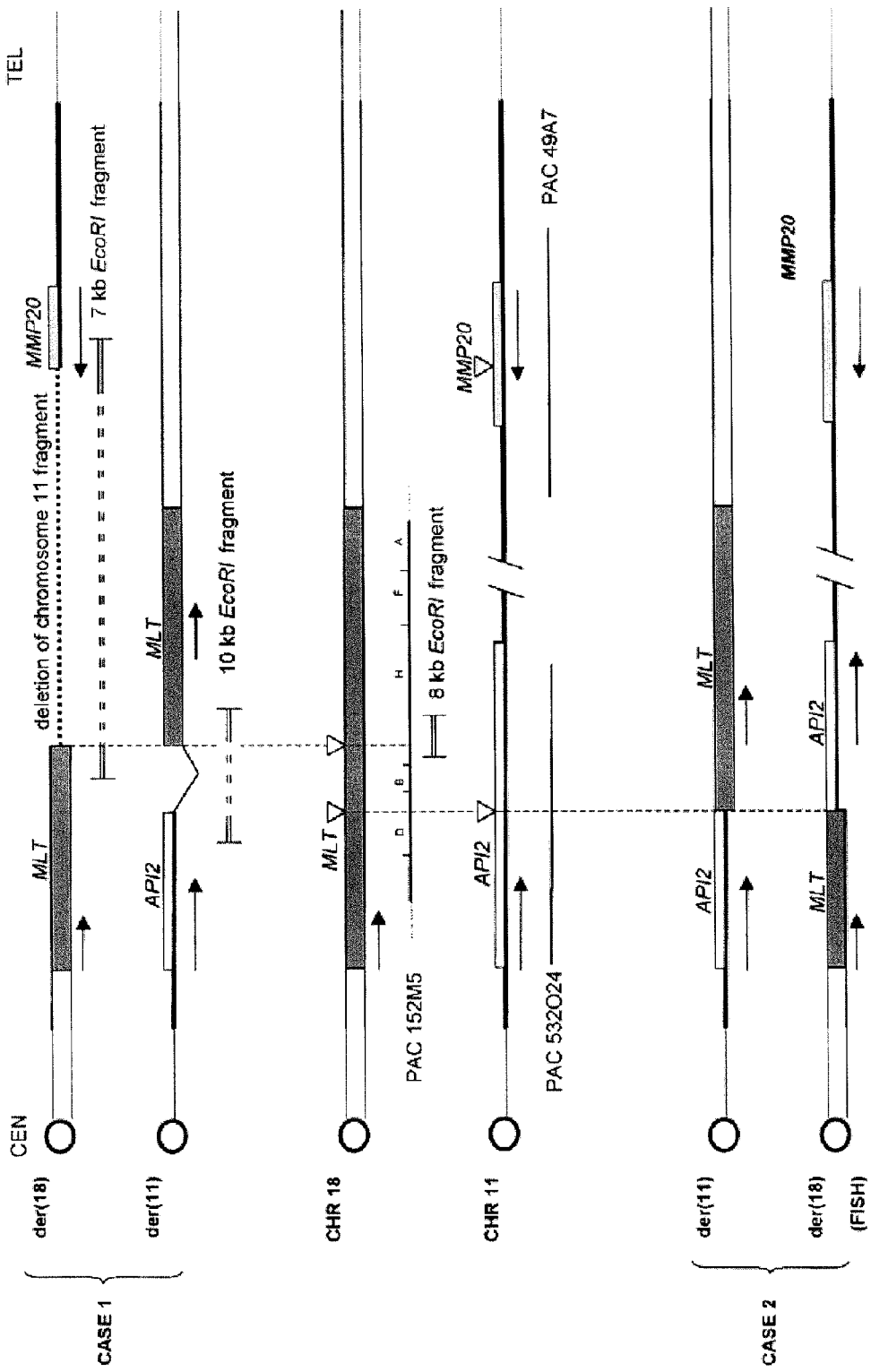
FIG. 2A-B: Molecular structure of the t(11;18). The genomic structure of the t(11;18) is shown in panel A. In the center, the MLT gene is shown as the darkly shaded area on the normal 18q; API2 and MMP20 are shown respectively as an open rectangle and a light grey rectangle on the normal 11q (not drawn to scale). Below each gene, the PAC isolated for this gene is shown. For PAC 152M5, the positions of the different BamHI fragments used for FISH experiments are indicated. On top, the rearrangement in case 1 is illustrated: the der(11) fuses the 5' end of API2 to the 3' end of MLT, while on the der(18), as a result from the cryptic deletion of chromosome 11, the 5' end of MLT is fused to the 5' end of MMP20. The transcriptional orientation of each gene is indicated by an arrow below each chromosome, showing that on the der(18), MLT and MMP20 do have an opposite transcriptional orientation. The genomic fusion fragments which were cloned respectively from the der(11) and the der(18) are indicated by the double lines. Below the rearrangement of case 2 is shown: the der(11) fuses 5' API2 to 3' MLT. The breakpoint in API2 is identical to the one in case 1; the breakpoint in MLT occurred upstream of the breakpoint in case 1 (see 2B). FISH experiments suggest that the der(18) is the balanced reciprocal of the der(11). The localizations of all breakpoints are indicated on the normal chromosomes by open triangles.

From the 9 YACs assigned to 18q21.1-22, five hybridized centromeric and two (including A153A6 containing the BCL2 gene) telomeric to the translocation breakpoint (see FIG. 1). The hybridization signals of YACs 949B6 and 817C6 were split by the translocation in both cases. YAC 949B6 contains 3 ordered STSs (cen-D18S887-D18S1055-D18S1129-tel). FISH experiments with PAC clones isolated for these STSs positioned the chromosome 18 breakpoint in case 1 between D18S1055 and D18S1129. A walking strategy initiated from both markers led to the identification of PAC 205G9 and 152M5, which were shown to be split by the t(11;18) in both cases. The breakpoints were further narrowed down by FISH analysis with BamHI fragments subcloned from PAC 152M5 (FIG. 2A). In case 1, fragment H was split by the translocation, whereas in case 2, the breakpoint could be mapped to fragment D (FIGS. 3A-D).

Cloning of the Fusion Genes

In order to identify genes on chromosome 18q in the vicinity of the breakpoints, the sequences derived from short random subclones from the BamHI fragments D, B, H and F were compared to the nucleotide databases. Subclone F24, mapping telomeric to the breakpoint, contained a 178 bp fragment identical to a single EST (IMAGE cDNA clone 1420842, GenBank accession no. AA826328) that resembles a hypothetical *Caenorhabditis elegans* gene (F22D3.6, Acc. No. U28993). The presence of canonical 5' and 3' splice sequences flanking the 178 bp suggested that this represented an exon of a human gene. A second exon with similarity to the same *C. elegans* gene product was predicted by computer analysis of subclone B9, located centromerically to the breakpoint in case 1. RT-PCR experiments confirmed that both exons were part of the same human transcript and indicated the disruption of this gene (named MLT for MALT-Lymphoma associated Translocation) by the translocation in case 1.

Figure 2B:
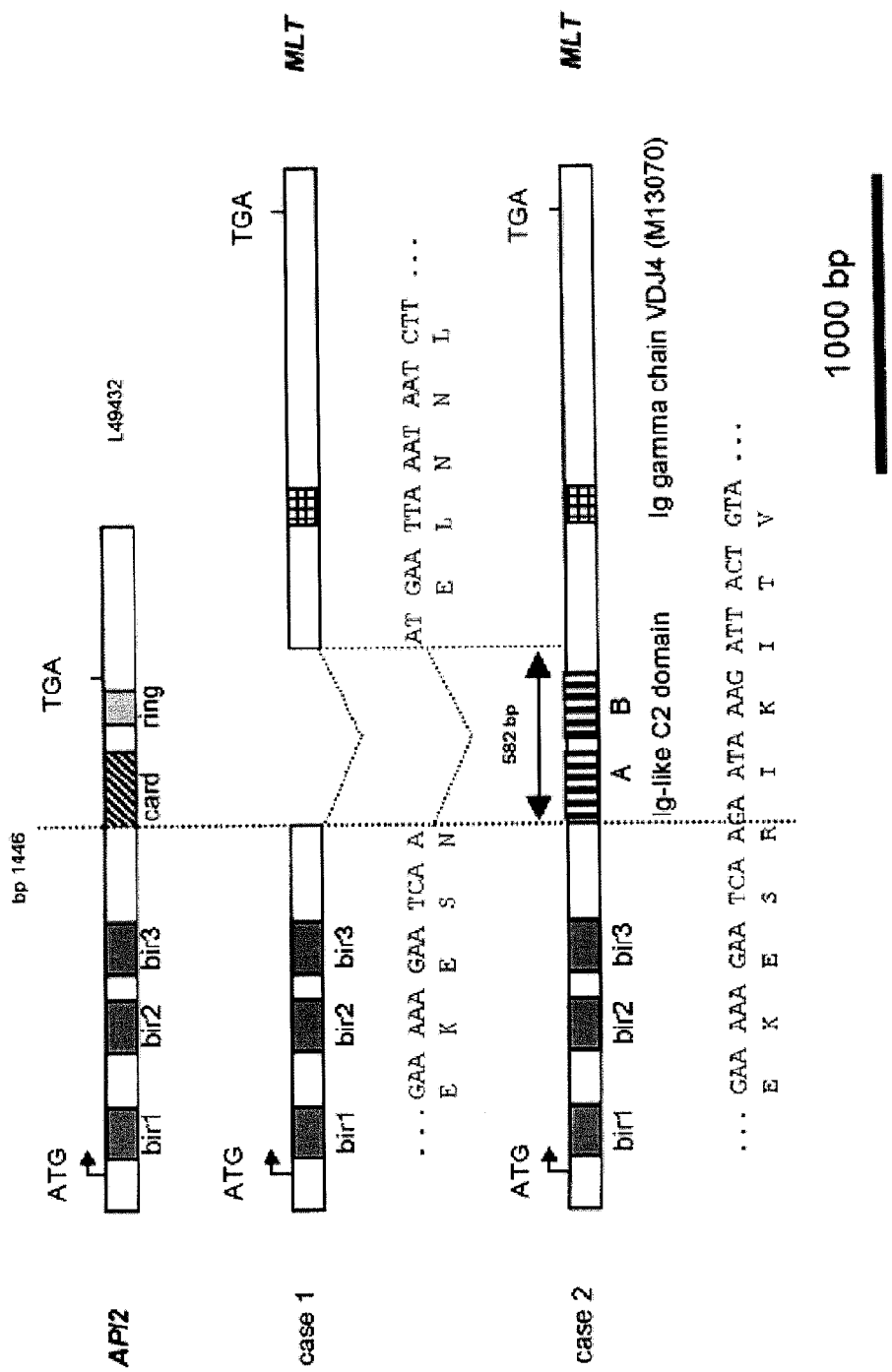
Figure 3A:
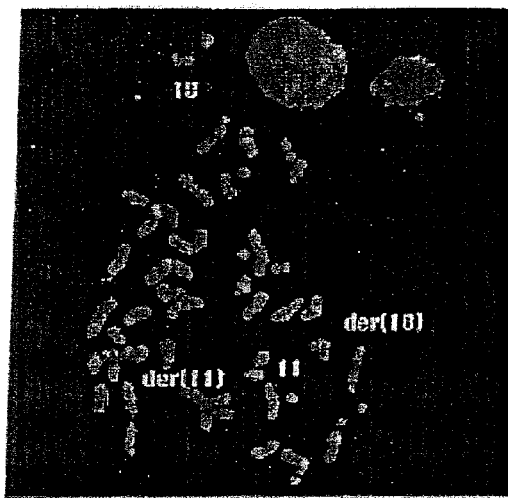
Figure 3B:
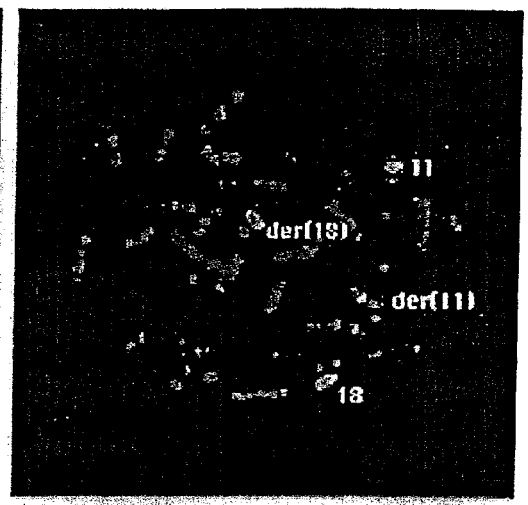
Figure 3C:
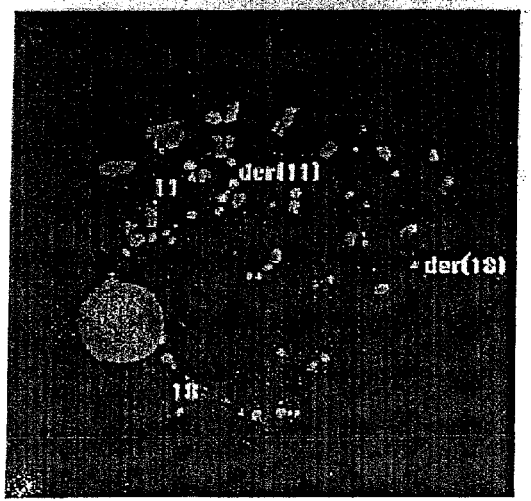
Figure 3D:
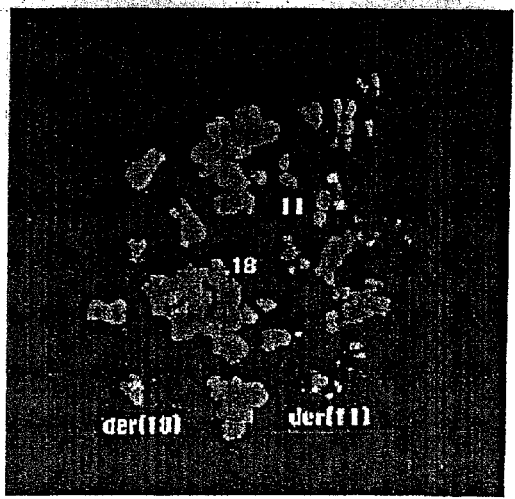

To identify an eventual chromosome 11 fusion partner for MLT, cDNA transcribed from RNA of case 1 was then used in 5' RACE experiments with two nested primers (MLTr1 and r2) derived from MLT sequences telomeric to the breakpoint. The amplification products were cloned and eight clones with an average insert length of 800 bp were sequenced. Five clones contained only MLT sequences. The three remaining clones showed a fusion of MLT sequences to the 5' part of the API2 gene, an inhibitor of apoptosis mapped to chromosome 11q22. The API2 protein contains three copies of the baculovirus IAP repeat (BIR) at its amino-terminus and a caspase recruitment domain or CARD[30] followed by a carboxy-terminal zinc binding RING finger domain.[31] The chimeric API2-MLT transcript contains base pairs 1-1446 of API2 (Genbank accession no. L49432) fused in frame with bp 583 of the partial MLT cDNA (Genbank accession no. AF130356). At the protein level, the first 441 AA of API2, containing the 3 BIR domains, are fused to the carboxy-terminal part of MLT (FIG. 2B).

Primers derived from the API2 and MLT cDNA sequences (M&M) were then used to confirm this fusion directly by RT-PCR. An amplification product with the expected size (445 bp) and sequence was obtained for patient 1, confirming the existence of the chimeric API2-MLT transcript. In contrast, using the same primers, a 1000 bp RT-PCR product was obtained with the RNA sample of the second patient (FIG. 4A). Sequence analysis of the cloned product again confirmed an API2-MLT fusion with a continuous open reading frame. The breakpoint in the API2 gene occurred at the same position as described for patient 1. The chimeric cDNA, however, contained an additional 582 bp MLT sequence in agreement with the more centromeric localization of the 18q breakpoint in this case as defined by FISH (FIG. 2B).

To complete the sequence of the chimeric mRNA, 3' RACE experiments were performed. The consensus cDNA sequences for both API2/MLT fusions are shown in FIG. 5.

Absence of a Reciprocal MLT-API2 Transcript

To analyze the genomic events leading to the expression of a chimeric API2-MLT transcript, we cloned the genomic breakpoints of case 1. To this aim, an 8 kb EcoRI fragment spanning the breakpoint was subcloned from fragment H. Southern hybridization with the 5' and the 3' end fragments of this clone detected rearranged EcoRI fragments of respectively 6 kb containing the 5' end of MLT and 10 kb containing the 3' end of MLT (FIG. 4B). Long-distance inverse PCR[32] was used to amplify the genomic chromosome 11 sequences present in both chimeric fragments and PAC clones corresponding to these chromosome 11 sequences were isolated. To our surprise, two independent sets of PAC clones were obtained. PAC 532024 was isolated using chromosome 11 sequences derived from the der(11). This PAC was shown to contain the 5' end of API2. FISH experiments with this PAC yielded signals on the normal 11 and the der(11) of case 1. PAC 49A7, obtained with chromosome 11 sequences derived from the der(18), however, did not contain API2 and sequencing showed that this clone contained the MMP20 gene instead (FIG. 2B). FISH experiments with this clone on case 1 resulted in fluorescent signals on the normal 11 and the der (18). Taken together, these data show that, in case 1, the t(11;18) is associated with a cryptic deletion of chromosome 11 sequences distal to the breakpoint, resulting in the absence of an MLT-API2 fusion. These data are in agreement with a localization of the MMP gene cluster telomeric to API2. As the exact distance is not known, we cannot estimate the size of the deletion. Sequencing of the der(18) fusion fragment showed that the MLT gene and the MMP20 gene are on opposite strands of the genome, thereby excluding the expression of an MLT-MMP20 transcript. FISH experiments on case 2 detected a signal for the PAC 532024 on the normal 11, the der(11) and the der(18) consistent with the occurrence of a balanced translocation and a breakpoint in API2. PAC 49A7 yielded fluorescent signals on the normal 11 and the der(18) consistent with the localization of the MMP20 gene distally to API2.

2. Evaluation of the Oncogenic Properties of the API2-MLT Fusion

Two strategies are applied to evaluate the oncogenic properties of the API2-MLT fusion in vivo.

In a first approach, we generate via a bone marrow transplant ("BMT") mice that express the API2-MLT fusion in their bone marrow cells. Lethally irradiated recipient mice are rescued by transplantation with donor bone marrow that are earlier retrovirally infected with a construct that expresses the API2-MLT fusion protein.

In a second approach, the API2-MLT fusion is introduced in a germline of mice through a human chromosomal vector (HCV). After incorporation of an API2-MLT fusion construct in the HCV via Cre-mediated homologous recombination in hamster cells, the vector is shuffled via microcell-mediated chromosome transfer to mouse ES cells for the generation of transchromosomal (transgenic) mice. B-cell specific expression of the API2-MLT fusion protein is achieved by using a B-cell specific promoter or by removal of a repressor element via a recombinase-mediated system driven by a B-cell specific promoter.

The mice models are used to assess the role of antigen triggering in the development and growth of gastric MALT lymphomas by infection with *Helicobacter felis*. Mice developing lymphoma provide the appropriate model to evaluate antibiotic therapies and therapies based on immune responses to the fusion protein.

3. Structure of the MLT Gene and Molecular Characterization of the Genomic Breakpoint Junctions in the t(11;18)(q21;q21) of Marginal Zone B-cell Lymphomas of MALT Type The present example relates to the characterization of the genomic organization of the MLT gene. The information is used to amplify the genomic breakpoint junctions for five MALT-type lymphomas with t(11;18)(q21;q21). Sequences near the breakpoint junctions do not yield evidence for the participation of site-specific recombinases or Alu-mediated homologous recombination in the generation of the t(11;18). Clustering of the breakpoints in intron 7 of API2 and the consistency of "in-frame" API2-MLT fusions therefore point to a selective advantage associated with these fusions which leads to their clonal outgrowth.

Materials and Methods

Patients

Five patients with gastric marginal zone B-cell lymphoma of MALT-type were investigated. The t(11;18) was confirmed by RT-PCR analysis for the API2-MLT fusion transcript (Baens et al. 2000). Cases 4 and 1 are cases 1 and 2 respectively of a previous study (Dierlamm et al. 1999). The features of the API2-MLT fusions for these five cases are depicted in FIG. 6B. Genomic DNA was extracted by using a standard isolation procedure (Sambrook et al. 1989) from 5 sections of 25 microns thick, taken from a frozen tissue block comprising the lymphoma.

The Genomic Structure of MLT

A fetal kidney cDNA library in λgt11 was screened with a 5' MLT probe to determine the full open reading frame of the MLT gene. MLT cDNAs for the entire open reading frame were used as probes on high-density filters containing 1 kb subclones of PAC 152M5. Purified PAC DNA was sonicated and the ends were blunted by successive treatment with respectively T4 DNA polymerase (AP Biotech, Uppsala, Sweden) and Klenow DNA polymerase (AP Biotech) in the presence of the 4 dNTPs. The fraction between 800 and 1500 bp was gel-purified (Qiaquick Gel Extraction, Qiagen, Hilden, Germany) and cloned into pUC18, linearized with SmaI and dephosphorylated (AP Biotech). Subclones identified by the MLT cDNA probes were sequenced to determine the exon-intron junctions. A vectorette PCR approach (Riley et al. 1990) was applied to amplify exon-intron boundaries absent in the subclone library.

Nucleotide sequencing reactions were carried out by dideoxynucleotide chain-termination with FITC-dATP or fluorescently labeled primers and analyzed on an Automated Laser Fluorescence sequencer (AP Biotech). Sequences were aligned with the Seqman software (DNAstar Inc.). Repeatmasker software developed by the University of Washington was used to identify repetitive elements.

Characterization of the Genomic API2-MLT and MLT-API2 Fusion Fragments

Nested or heminested amplification was performed using the Expand Long Template PCR System according to the manufacturer's recommendations (Roche Diagnostics, Mannheim, Del.). Primers used for amplification are summarized in Table 2. PCR amplification products were gel-purified (Qiaquick Gel Extraction, Qiagen), phosphorylated with T4 polynucleotide kinase (AP Biotech) and sonicated, and the fraction between 800 and 1500 bp was gel purified and cloned in pUC18/SmaI/BAP (AP Biotech). Intron 7 of API2 was amplified using primers API2-1374f and API2-1546r with as template DNA of PAC 523024, containing the API2 gene. Subcloning and sequencing was performed as described above. The genomic API2-MLT and MLT-MMP20 fusion fragments of case 4 were characterized in a previous study (Dierlamm et al. 1999).

Results

The Genomic Structure of the MLT Gene

The present invention discloses an MLT consensus cDNA sequence of 2491 bp (Genbank Accession number AF130356). A fetal kidney cDNA library was screened with a 5' cDNA probe and two hybridizing clones were identified. Sequence analysis revealed additional 5' sequences with an "in frame" ATG start codon at position 165 (Genbank Accession number AF130356). To determine the genomic organization of MLT, we generated a 1 kb subclone library of PAC 152M5 containing the MLT gene. Southern hybridizations confirmed the presence of 5' and 3' MLT sequences in this PAC clone. MLT cDNAs were used as probes on high-density filters containing the 1 kb subclones of PAC 152M5. Sequence analysis of hybridizing clones yielded the flanking intron sequences for all exons except exon 14 (3' acceptor of preceding intron missing). A vectorette PCR approach (Riley et al. 1990) was applied to characterize the missing boundary for exon 14. Base pairs 1-373 of the consensus cDNA sequence belong to exon 1 and show a high GC content (78%) with 48 CpG dinucleotides and recognition sequences for several rare cutting restriction enzymes (SacII, NarI, NaeI). In total, 17 exons all flanked by canonical splice donor and acceptor sites were identified (Table 1). The size of the introns was estimated by long range PCR with exon specific primers and/or restriction mapping. It shows that the MLT gene is approximately 80 kb in size (Table 1 and FIG. 6A).

The Genomic Breakpoint Junctions for 5 MALT-Type Lymphomas with t(11;18)

Five marginal zone B-cell lymphomas of MALT-type were selected from 11 cases identified with an API2-MLT fusion as part of large screening of gastric lymphomas (Baens et al. 2000). All 11 cases had their chromosome 11 breakpoint in the 5 kb intron between exon 7 and 8 of API2 (exon numbering according to Young et al. 1999). The genomic structure of MLT shows that the chromosome 18 breakpoint in these cases occurs upstream of exon 3, 5, 8 or 9 respectively and that the intron sizes permit amplification of the genomic fusion fragments using API2 and MLT exon primers (Table 2). Genomic DNA extracted from a frozen tissue block comprising the lymphoma was used as a template. Nested or heminested amplification yielded the genomic API2-MLT and MLT-API2 amplification products for all cases, except for case 2 where no MLT-API2 fragment could be amplified (Table 2). All fragments were partially sequenced until the breakpoint junctions were detected by comparison with the intron 7 sequence of API2 (Acc. No. AF178945). The sequence of the latter was determined from a 5 kb PCR fragment amplified from PAC 532024 with primers for exon 7 and 8 of API2 (Table 2). Sequences fused to API2 were then used to screen high-density filters containing the 1 kb subclones of PAC 152M5 to obtain the MLT sequences flanking the breakpoint.

The genomic breakpoints on chromosome 11 are scattered in intron 7 of API2 (FIG. 7A). Sequence analysis of the der(18) junction showed that the MLT gene is fused to MMP20 (Matrix MetalloProteinase 20). However, both genes are transcribed in opposite orientations which exclude the expression of an MLT-MMP20 fusion transcript. Sequence analysis of the API2-MLT fusion further indicated a deletion (2.3 kb) of chromosome 18 sequences (FIG. 7B). Deletions of chromosome 18 sequences were also observed for case 5 (350 bp) and case 3 (around 5 kb), in the latter case simultaneously with a small deletion of chromosome 11 sequences (53 bp) (FIG. 7B). No MLT-API2 amplification product was obtained for case 2. Based on the position of the der(11) breakpoint, the expected fragment is at most 5 kb and thus well within amplification range, which suggests a deletion of chromosome 11 sequences including exon 8 of API2. The latter is supported by FISH experiments with PAC 166G16 for API2 which yielded hybridization signals on the normal chromosome 11 and the der(11), but not the der(18). Identical FISH results were previously obtained for case 4 where the translocation was associated with a deletion of chromosome 11 sequences (>200 kb), which explains the absence of hybridization signals on the der(18) (Dierlamm et al. 1999). Only the translocation in case 1 is not associated with chromosomal loss (FIG. 7B).

Characteristic Sequences Near the Breakpoints

Computer-based FINDPATTERN® searches were performed to identify sequence motifs that might reveal a common mechanism for DNA breakage and rejoining. In lymphoid neoplasms, the presence of heptamer-nonamer recombination signals at or near the breakpoints suggests the involvement of V(D)J recombinase activity in the illegitimate recombination events leading to these translocations (Tycko and Sklar 1990). We did not find appropriate antigen receptor gene-like signals within the chromosome 11 and 18 sequences flanking the breakpoint junctions. The absence of non-template N nucleotides at the fusion junctions, characteristic for V(D)J recombination, further argues against its involvement.

Several other sequence motifs that could potentially infer recombination or genetic instability leading to chromosomal translocation have been reported, such as the DNA topoisomerase II binding and cleavage site (Negrini et al. 1993; Gu et al. 1994; Domer et al. 1995) χ-like sequences (Wyatt et al. 1992), the translin-binding consensus sequence (Jaeger et al. 1993; Aoki et al. 1995) and alternating polypurine-polypyrimidine stretches (Boehm et al. 1989; Thandla et al. 1999; Wiemels and Greaves 1999; Thandla et al. 1999; Wiemels and Greaves 1999). None of these sites were consistently present near the breakpoint junctions. An 18/18 bp match for the topoisomerase II consensus sequence was only observed for case 1. Degenerated sequences (15 to 16 bp match on 18) were identified on one or both participating chromosomes for 4 out of 5 cases, but their position relative to the breakpoint does not imply any causality. Based on the same criteria, a recombination event mediated by χ-like elements could be excluded. Furthermore, no regions homologous to the Translin-binding consensus sequence or with alternating polypurine/polypyrimidine stretches were apparent.

Homologous recombination between human Alu repeats located on the same or different chromosomes has been reported to cause chromosomal translocations (Jeffs et al. 1998; Strout et al. 1998). Alu repeats are also often observed in the vicinity of breakpoints and it is speculated that their mutual attraction juxtaposes these different chromosomal regions and in this way facilitates recurrent rearrangements between them (Obata et al. 1999). Repetitive sequences near the breakpoint junctions were identified using REPEATMASKER® and are summarized in FIGS. 7A and B. In two cases (4 and 5), the breakpoint in intron 7 of API2 occurred in an AluSx repeat, although a different one, but no AluSx sequences were found close to the breakpoint site on chromosome 18. Case 1 had a breakpoint in a copy of an AluSx repeat on chromosome 18 but the break in intron 7 of API2 was 558 bp upstream of the second AluSx repeat. For the remaining 2 cases (2, 3), AluSx repeats were detected close to the breakpoints on both chromosomes. For case 2, only the der(11) was characterized as no MLT-API2 amplification product was obtained. The breakpoint was located 400 bp downstream from an AluSx repeat on chromosome 11 and 52 bp upstream from an AluSx repeat in intron 4 of MLT. The der(11) breakpoint for case 3 was located 291 bp upstream from an AluSx repeat on chromosome 11 and 160 bp downstream from an AluSx on chromosome 18. Due to deletions affecting both chromosomes, the der(18) breakpoint was situated 238 bp upstream from an AluSx on chromosome 11 and in an AluY repeat in intron 4 of the MLT gene (FIG. 7B).

TABLES

[0068] Table 1: The exon-intron boundaries of the human *MLT* gene.

| exon No. | Location[a] | size | 3' end of the exon | 5' end of the intron | Intron size (kb) | 3' end of the intron | 5' end of the next exon |
|---|---|---|---|---|---|---|---|
| 1 | 1-373 | 373 | CGC CTC AG | GTgagc (SEQ ID NO:9) | 10 | tctttctgttgctttcAG | T TGC CTA (SEQ ID NO:10) |
| 2 | 374-540 | 167 | CCC CCA G | GTaggt (SEQ ID NO:11) | 15 | tttttttttttttttAG | GA ATA AAG (SEQ ID NO:12) |
| 3 | 541-662 | 122 | AAT AAA GAG | GTaatt (SEQ ID NO:13) | 4 | tcttattgatcttcacAG | ATT CCA AAT (SEQ ID NO:14) |
| 4 | 663-813 | 151 | TTC CAG A | GTaagt (SEQ ID NO:15) | 9 | tttttctttaattttaAG | GA AGT GTT (SEQ ID NO:16) |
| 5 | 814-992 | 179 | CTA TAC ATG | GTagga (SEQ ID NO:17) | 0.4 | gttctaatattgatatAG | GTG CCT TAT (SEQ ID NO:18) |
| 6 | 993-1089 | 97 | ATC ATA G | GTaaga (SEQ ID NO:19) | 0.9 | tgttttttctgaaacaAG | GA AGA ACA (SEQ ID NO:20) |
| 7 | 1090-1122 | 33 | ACT GAA G | GTagtg (SEQ ID NO:21) | 5.5 | tctcttacttttgttttAG | AT GAA TTA (SEQ ID NO:22) |
| 8 | 1123-1149 | 27 | CAT CCT G | GTgagt (SEQ ID NO:23) | 1.8 | tttttatctttgtatAG | AT AAT AAA (SEQ ID NO:24) |
| 9 | 1150-1182 | 33 | CCT TTG G | GTgagt (SEQ ID NO:25) | 7 | tttctttttttttcaaAG | CG AAG GAC (SEQ ID NO:26) |
| 10 | 1183-1386 | 204 | GTA TAT G | GTaaga (SEQ ID NO:27) | 11 | tatttttccctcttttcAG | GG TTA TTA (SEQ ID NO:28) |
| 11 | 1387-1564 | 178 | AGG AAA AG | GTaagt (SEQ ID NO:29) | 0.7 | tccgcctcccttaaatAG | A AAT GAC (SEQ ID NO:30) |
| 12 | 1565-1639 | 75 | TAT GCC AC | GTaaga (SEQ ID NO:31) | 0.9 | tcttttctatttttaAG | G TGT CAA (SEQ ID NO:32) |
| 13 | 1640-1767 | 128 | GCA GAA G | GTaaaa (SEQ ID NO:33) | 7 | tattttcatatcttttAG | AT ATG GGT (SEQ ID NO:34) |
| 14 | 1768-1917 | 150 | GCT CAT G | GTacgg (SEQ ID NO:35) | 2 | cttattgttcttttcAG | AA CTT CCA (SEQ ID NO:36) |
| 15 | 1918-2075 | 158 | TTT CCA CTT | GTgagt (SEQ ID NO:37) | 1.5 | taattttttttttacAG | GAT CTA GAT (SEQ ID NO:38) |
| 16 | 2076-2201 | 126 | AAA TTA AAG | GTtact (SEQ ID NO:39) | 1.5 | gattttttcctttcAG | GAA CAT CTA (SEQ ID NO:40) |
| 17 | 2202-2828 | 627 | TGA stop | | | | |

[a]: numbering according to *MLT* accession number AF130356.

TABLE 2

PCR primers used for long distance amplification of API2-MLT and MLT-API2 genomic fusions.

| API2-MLT | Primer | Locus | Size (kb) | Sequence | |
|---|---|---|---|---|---|
| 1r | API2-1266f | Exon 7 | | 5'-ATTAATGCTGCCGTGGAAAT | (SEQ ID NO: 41) |
| 2r | API2-1301f | Exon 7 | | 5'-CCTGGTAAAACAGACAGTTCAGA | (SEQ ID NO: 42) |
| case 1 1r | MLT-i2r1 | Intron 2 | 8 | 5'-CAGGTGGTGGATAACGTGGAGTTT | (SEQ ID NO: 43) |
| 2r | MLT-i2r2 | Intron 2 | | 5'-CACAAATCTGCCTGGCCAGAGAAG | (SEQ ID NO: 44) |
| case 2/3 1r | MLT-984r | Exon 5 | 10/7 | 5'-GCTTTTTGGTCTCATGTGTTAATG | (SEQ ID NO: 45) |
| 2r | MLT-929r | Exon 5 | | 5'-AATAGGGCTTCCAACAGCAA | (SEQ ID NO: 46) |
| case 4 1-2r | MLT-1147r | Exon 8 | 5 | 5'-GGATGACCAAGATTATTTAATTCA | (SEQ ID NO: 47) |
| case 5 1-2r | MLT-1181r | Exon 9 | ~1 | 5'-CAAAGGCTGGTCAGTTGTTTG | (SEQ ID NO: 48) |

| MLT-API2 | Primer | Locus | | Sequence | |
|---|---|---|---|---|---|
| 1r | API2-1684r | Exon 8 | | 5'-AACACAGCTTCAGCTTCTTGC | (SEQ ID NO: 49) |
| 2r | API2-1546r | Exon 8 | | 5'-TTAATAATTCCGGCAGTTAGTAGAC | (SEQ ID NO: 50) |
| case 1 1r | MLT-i2f1 | Intron 2 | | 5'-GGTTGAGCTTGGAAAGACAAAGG | (SEQ ID NO: 51) |
| 2r | MLT-i2f2 | Intron 2 | 6 | 5'-ACCTGATGCACTCTATTTTACGTGG | (SEQ ID NO: 52) |
| case 2/3 1r | MLT-717f | Exon 4 | | 5'-GCAGGCTTTTATGTCTGTCG | (SEQ ID NO: 53) |
| 2r | MLT-757f | Exon 4 | 2.2 | 5'-TTGAATTCAGCCAGTGGTCA | (SEQ ID NO: 54) |
| case 4 | previously done | 0.65 | (Dierlamm et al, 1999) | | |
| case 5 1r | MLT-i8f1 | Intron 8 | | 5'-CTTTTGTAAATAGCCACCACTAAGATT | (SEQ ID NO: 55) |
| 2r | MLT-i8f2 | Intron 8 | 5 | 5'-TTCCCACAATTCAGGGAGTACCAAA | (SEQ ID NO: 56) |

1r: first round primer
2r: second round primer
1-2r: first and second round primer

REFERENCE LIST

1. Tycko B, Sklar J: Chromosomal translocations in lymphoid neoplasia: a reappraisal of the recombinase model. Cancer Cells 2:1, 1990
2. Harris N L, Jaffe E S, Stein H, Banks P M, Chan J K, Cleary M L, Delsol G, De-Wolf-Peeters C, Falini B, Gatter K C: A revised European-American classification of lymphoid neoplasms: a proposal from the International Lymphoma Study Group. Blood 84:1361, 1994
3. De-Wolf-Peeters C, Pittaluga S, Dierlamm J, Wlodarska I, Van-den-Berghe H: Marginal zone B-cell lymphomas including mucosa-associated lymphoid tissue type lymphoma (MALT), monocytoid B-cell lymphoma and splenic marginal zone cell lymphoma and their relation to the reactive marginal zone. Leuk. Lymphoma 26:467, 1997
4. Hussell T, Isaacson P G, Crabtree J E, Spencer J: *Helicobacter pylori*-specific tumor-infiltrating T cells provide contact dependent help for the growth of malignant B cells in low-grade gastric lymphoma of mucosa-associated lymphoid tissue. J. Pathol. 178:122, 1996
5. Wotherspoon A C, Doglioni C, Diss T C, Pan L, Moschini A, de-Boni M, Isaacson P G: Regression of primary low-grade B-cell gastric lymphoma of mucosa-associated lymphoid tissue type after eradication of *Helicobacter pylori*. Lancet 342:575, 1993
6. Bayerdorffer E, Neubauer A, Rudolph B, Thiede C, Lehn N, Eidt S, Stolte M: Regression of primary gastric lymphoma of mucosa-associated lymphoid tissue type after cure of *Helicobacter pylori* infection. MALT Lymphoma Study Group. Lancet 345:1591, 1995
7. Qin Y, Greiner A, Trunk M J, Schmausser B, Ott M M, Muller H H: Somatic hypermutation in low-grade mucosa-associated lymphoid tissue-type B-cell lymphoma. Blood 86:3528, 1995
8. Tierens A, Delabie J, Pittaluga S, Driessen A, DeWolf P C: Mutation analysis of the rearranged immunoglobulin heavy chain genes of marginal zone cell lymphomas indicates an origin from different marginal zone B lymphocyte subsets. Blood 91:2381, 1998
9. Auer I A, Gascoyne R D, Connors J M, Cotter F E, Greiner T C, Sanger W G, Horsman D E: t(11;18)(q21;q21) is the most common translocation in MALT lymphomas. Ann. Oncol. 8:979, 1997
10. Clark H M, Jones D B, Wright D H: Cytogenetic and molecular studies of t(14;18) and t(14;19) in nodal and extranodal B-cell lymphoma. J. Pathol. 166:129, 1992
11. Dierlamm J, Pittaluga S, Wlodarska I, Stul M, Thomas J, Boogaerts M, Michaux L, Driessen A, Mecucci C, Cassiman J J, et al.: Marginal zone B-cell lymphomas of different sites share similar cytogenetic and morphologic features. Blood 87:299, 1996
12. Horsman D, Gascoyne R, Klasa R, Coupland R: t(11;18) (q21;q21.1): a recurring translocation in lymphomas of mucosa-associated lymphoid tissue (MALT)? Genes Chromosomes. Cancer 4:183, 1992
13. Kubonishi I, Sugito S, Kobayashi M, Asahi Y, Tsuchiya T, Yamashiro T, Miyoshi I: A unique chromosome translocation, t(11;12;18)(q13;q13;q12), in primary lung lymphoma. Cancer Genet. Cytogenet. 82:54, 1995
14. Ott G. Katzenberger T. Greiner A, Kalla J, Rosenwald A, Heinnich U, Ott M M, Muller H H: The t(11;18)(q21;q21) chromosome translocation is a frequent and specific aberation in low-grade but not high-grade malignant non-Hodgkin's lymphomas of the mucosa-associated lymphoid tissue (MALT-) type. Cancer Res. 57:3944, 1997
15. Robledo M, Benitez J, Rivas C, Martinez C P: Cytogenetic study of B-cell lymphoma of mucosa-associated lymphoid tissue. Cancer Genet. Cytogenet. 62:208, 1992
16. Whang P J, Knutsen T, Jaffe E, Raffeld M, Zhao W P, Duffey P, Longo D L: Cytogenetic study of two cases with lymphoma of mucosa-associated lymphoid tissue. Cancer Genet. Cytogenet. 77:74, 1994
17. Wotherspoon A C, Pan L X, Diss T C, Isaacson P G: Cytogenetic study of B-cell lymphoma of mucosa-associated lymphoid tissue. Cancer Genet. Cytogenet. 58:35, 1992
18. Leroux D, Seite P, Hillion J, Le-Marc'hadour F, Pegourie B B, Jacob M C, Larsen C J, Sotto J J: t(11;18)(q21;q21) may delineate a spectrum of diffuse small B-cell lymphoma with extranodal involvement. Genes Chromosomes. Cancer 7:54, 1993
19. Levine E G, Arthur D C, Machnicki J, Frizzera G, Hurd D, Peterson B, Gail P K, Bloomfield C D: Four new recurring translocations in non-Hodgkin lymphoma. Blood 74:1796, 1989
20. Griffin C A, Zehnbauer B A, Beschorner W E, Ambinder R, Mann R: t(11;18)(q21;q21) is a recurrent chromosome abnormality in small lymphocytic lymphoma. Genes Chromosomes. Cancer 4:153, 1992
21. Dierlamm J, Michaux L, Wlodarska I, Pittaluga S, Zeller W, Stul M, Criel A, Thomas J, Boogaerts M, Delaere P, Cassiman J J, De-Wolf-Peeters C, Mecucci C, Van-den-Berghe H: Trisomy 3 in marginal zone B-cell lymphoma: a study based on cytogenetic analysis and fluorescence in situ hybridization. Br. J. Haematol. 93:242, 1996
22. Rothe M, Pan M G, Henzel W J, Ayres T M, Goeddel D V: The TNFR2-TRAF signaling complex contains two novel proteins related to baculoviral inhibitor of apoptosis proteins. Cell 83:1243, 1995
23. Liston P, Roy N, Tamai K, Lefebvre C, Baird S, Cherton H G, Farahani R, McLean M, Ikeda J E, MacKenzie A, Korneluk R G: Suppression of apoptosis in mammalian cells by NAIP and a related family of IAP genes. Nature 379:349, 1996
24. Uren A G, Pakusch M, Hawkins C J, Puls K L, Vaux D L: Cloning and expression of apoptosis inhibitory protein homologs that function to inhibit apoptosis and/or bind tumor necrosis factor receptor-associated factors. Proc. Natl. Acad. Sci. U.S.A 93:4974, 1996
25. Dierlamm J, Wlodarska I, Michaux L, La Starza R: Successful Use of the Same Slide for Consecutive Fluorescence In Situ Hybridization Experiments. Genes Chromosomes. Cancer 16:261, 1996
26. Chumakov I M, Rigault P, Le G, I, Bellanne C C, Billault A, Guillou S, Soularue P, Guasconi G, Poullier E, Gros I, Belova M, Sambucy J-L, Susini L, Gervy P, Gilbert F, Beaufils S, Bui H, Massart C, De Tand M-F, Dukasz F, Lecoulant S, Ougen P, Perrot V, Saumier M, Soravito C, Bahouayila R, Cohen-Akenine A, Barillot E, Bertrand S, Codani J-J, Caterina D, Georges I, Lacroix B, Lucotte G, Sahbatou M, Schmidt C, Sangouard M, Tubacher E, Dib C, Fauré S, Fizames C, Gyapay G, Millaseau P, Nguyen S, Muselet D, Vignal A, Morissette J, Menninger J, Lieman J, Desai T, Banks A, Bray-Ward P, Ward D, Hudson T J, Gerety S S, Foote S, Stein L, Page D C, Lander E S, Weissenbach J, Le Paslier D, Cohen D: A YAC contig map of the human genome. Nature 377:175, 1995
27. Poetsch M, Weber M K, Plendl H J, Grote W, Schlegelberger B: Detection of the t(14;18) chromosomal translocation by interphase cytogenetics with yeast-artificial-chromosome probes in follicular lymphoma and nonneoplastic lymphoproliferation. J. Clin. Oncol. 14:963, 1996
28. Lengauer C, Green E D, Cremer T: Fluorescence in situ hybridization of YAC clones after Alu-PCR amplification. Genomics 13:826, 1992
29. Riley J, Butler R, Ogilvie D, Finniear R, Jenner D, Powell S, Anand R, Smith J C, Markham A F: A novel, rapid method for the isolation of terminal sequences from yeast artificial chromosome (YAC) clones. Nucleic Acids Res. 18:2887, 1990
30. Hofmann K, Bucher P. Tschopp J: The CARD domain: a new apoptotic signaling motif. Trends Biochem. Sci. 22:155, 1997
31. Saurin A J, Borden K L, Boddy M N, Freemont P S: Does this have a familiar RING? Trends Biochem. Sci. 21:208, 1996
32. Willis T G, Jadayel D M, Coignet L J, Abdul R M, Treleaven J G, Catovsky D, Dyer M J: Rapid molecular cloning of rearrangements of the IGHJ locus using long-distance inverse polymerase chain reaction. Blood 90:2456, 1997
33. Clem R J, Fechheimer M, Miller L K: Prevention of apoptosis by a baculovirus gene during infection of insect cells. Science 254:1388, 1991
34. Hay B A, Wassarman D A, Rubin G M: Drosophila homologs of baculovirus inhibitor of apoptosis proteins function to block cell death. Cell 83:1253, 1995
35. Roy N, Deveraux Q L, Takahashi R, Salvesen G S, Reed J C: The c-IAP-1 and c-IAP-2 proteins are direct inhibitors of specific caspases. EMBO J. 16:6914, 1997
36. Duckett C S, Nava V E, Gedrich R W, Clem R J, Van-Dongen J L, Gilfillan M C, Shiels H, Hardwick J M, Thompson C B: A conserved family of cellular genes related to the baculovirus iap gene and encoding apoptosis inhibitors. EMBO J. 15:2685, 1996
37. Ambrosini G, Adida C, Altieri D C: A novel anti-apoptosis gene, survivin, expressed in cancer and lymphoma. Nat. Med. 3:917, 1997
38. Deveraux Q L, Roy N, Stennicke H R, Van-Arsdale T, Zhou Q, Srinivasula S M, Alnemri E S, Salvesen G S, Reed J C: IAPs block apoptotic events induced by caspase-8 and cytochrome c by direct inhibition of distinct caspases. EMBO J. 17:2215, 1998
39. Du M, Singh N, Husseuin A, Isaacson P G, Pan L: Positive correlation between apoptotic and proliferative indices in gastrointestinal lymphomas of mucosa-associated lymphoid tissue (MALT). J. Pathol. 178:379, 1996
40. Greiner A, Seeberger H, Knorr C, Starostik P, Müller-Hermelinck H K: MALT-type B-cell lymphomas escape the censoring FAS-mediated apoptosis. Blood 92 Suppl.1: #1997, 1998 (abstr.)
41. Jain V K, Judde J G, Max E E, Magrath I T: Variable IgH chain enhancer activity in Burkitt's lymphomas suggests an additional, direct mechanism of c-myc deregulation. J. Immunol. 150:5418, 1993
42. Adida C, Crotty P L, McGrath J, Berrebi D, Diebold J, Altieri D C: Developmentally regulated expression of the novel cancer anti-apoptosis gene survivin in human and mouse differentiation. Am. J. Pathol. 152:43, 1998

Akagi T, Motegi M, Tamura A, Suzuki R, Hosokawa Y, Suzuki H, Ota H, Nakamura S, Morishima Y, Taniwaki M, Seto M: A novel gene, MALT1 at 18q21, is involved in t(11;18) (q21;q21) found in low-grade B-cell lymphoma of mucosa-associated lymphoid tissue. Oncogene 18: 5785-5794, 1999

Aoki K, Suzuki K, Sugano T, Tasaka T, Nakahara K, Kuge O, Omori A, Kasai M: A novel gene, Translin, encodes a recombination hotspot binding protein associated with chromosomal translocations. Nat. Genet. 10: 167-174, 1995

Aplan P D, Raimondi S C, Kirsch I R: Disruption of the SCL gene by a t(1;3) translocation in a patient with T cell acute lymphoblastic leukemia. J. Exp. Med. 176: 1303-1310, 1992

Baens M, Maes B, Steyls A, Geboes K, Marynen P, De Wolf-Peeters C: The product of the t(11;18), an API2-MLT fusion, marks nearly half of the gastro-intestinal MALT type lymphomas without large cell proliferation. Am. J. Pathol. 156:1433-1439

Baguley B C, Ferguson L R: Mutagenic properties of topoisomerase-targeted drugs. Biochim. Biophys. Acta 1400: 213-222, 1998

Bernard O A, Berger R: Molecular basis of 11q23 rearrangements in hematopoietic malignant proliferations. Genes Chromosomes. Cancer 13: 75-85, 1995

Boehm T, Mengle-Gaw L, Kees U R, Spurr N, Lavenir I, Forster A, Rabbitts T H: Alternating purine-pyrimidine tracts may promote chromosomal translocations seen in a variety of human lymphoid tumors. EMBO J. 8: 2621-2631, 1989

Chissoe S L, Bodenteich A, Wang Y F, Wang Y P, Burian D, Clifton S W, Crabtree J, Freeman A, Iyer K, Jian L, et al.: Sequence and analysis of the human ABL gene, the BCR gene, and regions involved in the Philadelphia chromosomal translocation. Genomics 27: 67-82, 1995

Dierlamm J, Baens M, Wlodarska I, Stefanova O M, Hernandez J M, Hossfeld D K, De-Wolf-Peeters C, Hagemeijer A, Van-den-Berghe H, Marynen P: The apoptosis inhibitor gene API2 and a novel 18q gene, MLT, are recurrently rearranged in the t(11;18) (q21;q21) p6ssociated with mucosa-associated lymphoid tissue lymphomas. Blood 93: 3601-3609, 1999

Domer P H, Head D R, Renganathan N, Raimondi S C, Yang E, Atlas M: Molecular analysis of 13 cases of MLL/11q23 secondary acute leukemia and identification of topoisomerase II consensus-binding sequences near the chromosomal breakpoint of a secondary leukemia with the t(4;11). Leukemia 9:1305-1312, 1995

Golub T R, Barker G F, Bohlander S K, Hiebert S W, Ward D C, Bray-Ward P, Morgan E, Raimondi S C, Rowley J D, Gilliland D G: Fusion of the TEL gene on 12p13 to the AML1 gene on 21q22 in acute lymphoblastic leukemia. Proc. Natl. Acad. Sci. U.S.A 92: 4917-4921, 1995

Gu Y, Alder H, Nakamura T, Schichman S A, Prasad R, Canaani O, Saito H, Croce C M, Canaani E: Sequence analysis of the breakpoint cluster region in the ALL-1 gene involved in acute leukemia. Cancer Res. 54: 2326-2330, 1994

Harris N L, Jaffe E S, Diebold J, Flandrin G, Muller-Hermelink H K, Vardiman J, Lister T A, Bloomfield C D: World Health Organization Classification of Neoplastic Diseases of the Hematopoietic and Lymphoid Tissues: Report of the Clinical Advisory Committee Meeting-Airlie House, Va., November 1997. J. Clin. Oncol. 17: 3835-3849, 1999

Jaeger U, Purtscher B, Karth G D, Knapp S, Mannhalter C, Lechner K: Mechanism of the chromosomal translocation t(14;18) in lymphoma: detection of a 45-Kd breakpoint binding protein. Blood 81: 1833-1840, 1993

Jeffs A R, Benjes S M, Smith T L, Sowerby S J, Morris C M: The BCR gene recombines preferentially with Alu elements in complex BCR-ABL translocations of chronic mycloid leukaemia. Hum. Mol. Genet 7: 767-776, 1998

Lochner K, Siegler G, Fuhrer M, Greil J. Beck J D, Fey G H, Marschalek R: A specific deletion in the breakpoint cluster region of the ALL-1 gene is associated with acute lymphoblastic T-cell leukemias. Cancer Res. 56: 2171-2177, 1996

Maes B, Baens M, Marynen P, De Wolf-Peeters C: The product of the t(11;18), an API2-MLT fusion, is an almost exclusive finding in marginal zone cell lymphoma of extranodal MALT-type. Ann. Oncol., in press Maraschin J, Dutrillaux B, Aurias A: Chromosome aberrations induced by etoposide (VP-16) are not random. Int. J. Cancer 46: 808-812. 1990

Mitelman F, Mertens F, Johansson B: A breakpoint map of recurrent chromosomal rearrangements in human neoplasia. Nat. Genet. 15 Spec No: 417-474, 1997

Negrini M, Felix C A, Martin C, Lange B J, Nakamura T, Canaani E, Croce C M: Potential topoisomerase II DNA-binding sites at the breakpoints of a t(9;11) chromosome translocation in acute myeloid leukemia. Cancer Res. 53: 4489-4492, 1993

Obata K, Hiraga H, Nojima T, Yoshida M C, Abe S: Molecular characterization of the genomic breakpoint junction in a t(11;22) translocation in Ewing sarcoma. Genes Chromosomes. Cancer 25: 6-15, 1999

Reichel M, Gillert E, Nilson I, Siegler G, Greil J, Fey G H, Marsehalek R: Fine structure of translocation breakpoints in leukemic blasts with chromosomal translocation t(4;11): the DNA damage-repair model of translocation. Oncogene 17: 3035-3044, 1998

Romana S P, Poirel H, Leconiat M, Flexor M A, Mauchauffe M, Jonveaux P, Macintyre E A, Berger R, Bernard O A: High frequency of t(12;21) in childhood B-lineage acute lymphoblastic leukemia. Blood 86: 4263-4269, 1995

Rosenwald A, Ott G, Stilgenbauer S, Kalla J, Bredt M, Katzenberger T, Greiner A, Ott M M, Gawin B, hner H, ller-Hermelink H K: Exclusive Detection of the t(11;18) (q21;q21) in Extranodal Marginal Zone B Cell Lymphomas (MZBL) of MALT Type in Contrast to other MZBL and Extranodal Large B Cell Lymphomas. Am. J. Pathol. 155: 1817-1821, 1999

Sambrook J, Fritsch E, Maniatis T: Molecular cloning: A laboratory manual. Cold Spring Harbor, N.Y.: Cold Spring Harbor Laboratory, 1989

Showe L C, Croce C M: The role of chromosomal translocations. Annu. Rev. Immunol. 5: 253-277, 1987

Strout M P, Marcucci G, Bloomfield C D, Caligiuri M A: The partial tandem duplication of ALL1 (MLL) is consistently generated by Alu-mediated homologous recombination in acute myeloid leukemia. Proc. Natl. Acad. Sci. U.S.A 95: 2390-2395, 1998

Thandla S P, Ploski J E, Raza E S, Chhalliyil P P, Block A W, de-Jong P J, Aplan P D: ETV6-AML1 translocation breakpoints cluster near a purine/pyrimidine repeat region in the ETV6 gene. Blood 93: 293-299, 1999

Toth G, Jurka J: Repetitive DNA in and around translocation breakpoints of the Philadelphia chromosome. Gene 140: 285-288, 1994

Tsujimoto Y, Gorham J, Cossman J, Jaffe E, Croce C M: The t(14;18) chromosome translocations involved in B-cell neoplasms result from mistakes in VDJ joining. Science 229: 1390-1393, 1985

Wiemels J L, Greaves M: Structure and possible mechanisms of TEL-AML1 gene fusions in childhood acute lymphoblastic leukemia. Cancer Res. 59: 4075-4082, 1999

Wyatt R T, Rudders R A, Zelenetz A, Delellis R A, Krontiris T G: BCL2 oncogene translocation is mediated by a chi-like consensus. J. Exp. Med. 175: 1575-1588, 1992

Young S S, Liston P, Xuan J Y, McRoberts C, Lefebvre C A, Korneluk R G: Genomic organization and physical map of the human inhibitors of apoptosis: HIAP1 and HIAP2. Mamm. Genome 10: 44-48, 1999

What is claimed is:

1. An isolated nucleotide sequence consisting of a nucleic acid encoding SEQ ID NO:60.

2. The isolated nucleotide sequence of claim 1, wherein said nucleotide sequence is fluorescently labeled.

3. An isolated nucleic acid consisting of the complement of the isolated nucleotide sequence of claim 1.

4. The isolated nucleic acid of claim 3, wherein said nucleic acid is fluorescently labeled.

5. An isolated RNA encoding amino acids 528-566 of SEQ ID NO:60.

6. A cDNA encoding amino acids 528-566 of SEQ ID NO:60.

7. A recombinant virus encoding amino acids 528-566 of SEQ ID NO:60.

* * * * *